United States Patent
Kishimoto et al.

(10) Patent No.: US 7,361,737 B2
(45) Date of Patent: Apr. 22, 2008

(54) MOUSE CXC CHEMOKINE RECEPTOR

(75) Inventors: Tadamitsu Kishimoto, 5-31, Nakano 3-chome, Tondabayashi-shi, Osaka 584 (JP); Takashi Nagasawa, Sakai (JP); Kazunobu Tachibana, Sakai (JP); Hisashi Iizasa, Kanazawa (JP); Nobuaki Yoshida, Kashiba (JP); Toshihiro Nakajima, Toyonaka (JP); Osamu Yoshie, Nishinomiya (JP)

(73) Assignees: Shionogi & Co., Ltd, Osaka (JP); Tadamitsu Kishimoto, Osaka (JP)

( * ) Notice: Subject to any disclaimer, the term of this patent is extended or adjusted under 35 U.S.C. 154(b) by 0 days.

(21) Appl. No.: 11/437,734

(22) Filed: May 22, 2006

(65) Prior Publication Data

US 2006/0211037 A1 Sep. 21, 2006

Related U.S. Application Data

(62) Division of application No. 09/367,052, filed as application No. PCT/JP97/00299 on Feb. 7, 1997, now Pat. No. 7,074,616.

(51) Int. Cl.
*C07K 14/00* (2006.01)
*C07K 14/47* (2006.01)
*C07K 14/705* (2006.01)
*C07H 21/00* (2006.01)
*C07H 21/04* (2006.01)

(52) U.S. Cl. ..................... 530/350; 536/23.5

(58) Field of Classification Search ............. None
See application file for complete search history.

(56) References Cited

FOREIGN PATENT DOCUMENTS

WO WO-97/28258 A1 8/1997

OTHER PUBLICATIONS

Bleul et al., "A highly efficacious lymphocyte chemoattractant, stromal cell-derived factor 1 (SDF-1)," Journal of Experimental Medicine, vol. 184, No. 3, pp. 1101-1109 (Sep. 1996).*
Gotoh et al., "Increase of R5 HIV-1 infection of CCR5 expression in T cells treated with high concentrations of CXCR4 antagonists and SDF-1," Journal of Infection and Chemotherapy, vol. 7 No. 1, pp. 28-36 (Mar. 2001).*
Loetscher et al., "Cloning of a human seven-transmembrane domain receptor, LESTR, that is highly expressed in leukocytes," Journal of Biological Chemsitry, vol. 269 No. 1, pp. 232-237 (Jan. 1994).*
Nagasawa, Takashi et al., Proc. Natl. Acad. Sci. USA, 1996, 93 (25), 14726-14729.
Heesen, Michael et al., J. Immunol., 1996, 157(12), 5455-5460.
Database EMBL, EBI Online, Hinxton, Cambridgeshire, U.K., Database accession No. D99581 (XP002223233), abstract of Moepps et al., "*M. musculus* gene encoding leukocyte-derived seven transmembrane domain receptor, strain B6" (Nov. 1, 1996).
Joanne F. Berson et al., J. Virol., vol. 70, No. 9, pp. 6288-6295, Sep. 1996.
Database EMBL, EBI Online, Hinxton, Cambridgeshire, U.K., Database accession No. D87747 (XP002223286), abstract of T. Nagasawa, "*Mus musculus* mRNA for murine CXCR-4, complete cds.", Jan. 12, 1997.
Bowie et al., *Science*, vol. 24, pp. 1306-1310 (1990).
Bieniasz et al., Journal of Virology, vol. 71, No. 9. pp. 7097-7100 (Sep, 1997).
Lorez et al., *Aids Research and Human Retroviruses*, vol. 8, No. 12, pp. 2063-2071 (1992).
Ashorn et al., *Journal of Virology*, vol. 64, pp. 2149-2156 (1990).
Estelle Oberlin et al.; Letters to Nature; vol. 382; pp. 833-835; XP002028004.
Alignment of DNAs encoding mouse and human CXCR-4; EMBOSS-Align; Matrix DNA full, no date avail.
Y. Feng et al., *Science*, vol. 272, (1996), pp. 872-877.
Lapidot, "Mechanism of Human Stem Cell Migration and Repopulation of NOD/SCID and B2mnull NOD/SCID Mice: the Role of SDF-1/CXCR4 Interactions", Annals of the New York Academy of Sciences, vol. 938, pp. 83-95, 2001.

\* cited by examiner

*Primary Examiner*—Zachariah Lucas
(74) *Attorney, Agent, or Firm*—Birch Stewart Kolasch & Birch LLP

(57) ABSTRACT

The present invention pertains to a DNA encoding a polypeptide including an entire sequence of the amino acid sequence as shown by SEQ ID NO: 2 or a partial sequence thereof, or a polypeptide including the polypeptide described above, wherein any of the polypeptides has an activity of a receptor capable of binding to a murine PBSF/SDF-1; a polypeptide encoded by the DNA described above, wherein the polypeptide has an activity of a receptor capable of binding to a murine PBSF/SDF-1; cells expressing the polypeptide described above and a human CD4 protein; and a method of screening an AIDS onset inhibitor or an HIV-1 infection inhibitor, characterized by the use of the cells described above. According to the present invention, there can be provided a novel murine CXC chemokine receptor gene, a method of screening an HIV-1 infection inhibitor, and the like, each of which is useful in studies of a therapeutic agent for AIDS and the functional mechanism of HIV-1 infection.

2 Claims, 14 Drawing Sheets

```
CTCGGTGTCCTCTTGCTGTCCAGCTCTGCAGCCTCCGGCGGCCCCTCCCCACCGCCATGGACGCCAAGGTCGTCGCC  (79)
                                                        MetAspAlaLysValValAla
                                                        - - - - - - - - - - -

GTGCTGGCCCTGGTGCTGGCCGCGCTCTGCATCAGTGACGGTAAACCAGTCAGCCTGAGCTACCGATGCCCCTGCCGGTTC
ValLeuAlaLeuValLeuAlaAlaLeuCysIleSerAspGlyLysProValSerLeuSerTyrArgCysProCysArgPhe
- - - - - - - - - - - - - - - - - - - - - - - - - - - - - - - - - - - - - -   *  (241)

TTCGAGAGCCACATCGCCAGAGCCAACGTTCAAGGCATCTGAAAATCCTCAAACTGTGCCCTTCAGATTGTTGCA
PheGluSerHisIleAlaArgAlaAsnValLysHisLeuIleLeuAsnThrProAsnCysAlaLeuGlnIleValAla
                                                                            *

CGGCTGAAGAAGAACAACAACAGACAAGTGTGCATTGACCCGGAATTAAAGTGGATCCAAGAGTACCTGGAGAAAGCTTTAAAC
ArgLeuLysLysAsnAsnAsnArgGlnValCysIleAspProLysLeuLysTrpIleGlnGluTyrLeuGluLysAlaLeuAsn  (403)

AAGTAAGCACAACAGCCCAAAGGACTTTCCAGTAGACCCCCGAGGAAGGCTGACATCCGTGGGAGATGCAAGGGCAGTGGT
Lys
GGGGAGGAGGGCCTGAACCCTGGCCAGGATGGCCCGGGACAGCACTGACTGGGGTCATGCTAAGGTTTGCCAGCATAAA

GACACTCCGCCATAGCCATATGGTACGATATTGCAGCTTATATTCATCCCTGCCCGTGCACAATGGAGCTTTATA

ACTGGGGTTTTCTAAGGAATTGTATTACCCTAACCAGTTAGCTTCATCCCCATTCTCCTCATCCTTCATTTTAAA
```

Fig. 1

```
AAGCAGTGATTACTTCAAGGGCTGTATTCAGTTTGCTTTGGAGCTTCTCTTTGCCCTCTGGGCCTCTGGGCACAGTTATAGA
CGGTGGCTTTGCAGGGAGCCCCTAGAGAGAAACCTTCCACCAGAGCAGAGTCCGAGGAACGCTGCAGGGCTTGTCCTGCAGG
GGGCGCTCCTCGACAGATGCCTTGTCCTGAGTCAACACAAGATCCGGCAGAGGAGGCTCCTTATCCAGTTCAGTGCCAG
GGTCGGGAAGCTTCCTTTAGAAGTGATCCCTGAAGCTGTGCTCAGAGAACCCTTTCCTAGCCGTTCCTGCTCTCTGCTTGCC
                                                                             (1051)
TCCAAACGCATGCTTCATCTGACTTCCGCTTCTCACCTCTGTAGCCTGACGGACCAATGCTGCAATGGAAGGGAGGAGAGT
GATGTGGGGTGCCCCCTCCCTCTCTTCCCTTTGCTTCTCCTCACTTGGGCCCTTTGTGAGATTTTCTTTGGCCTCCTGT
AGAATGGAGCCAGACCATCCTGGATAATGTGAGAACATGCCTAGATTTACCCACAAAACACAAGTCTGAGAATTAATCATA
AACGGAAGTTTAAATGAGGATTTGGACTTTGGTAATTGTCCCTGAGTCCTATATATTTCAACAGTGGCTCTATGGGCTCTG
                                                                 ‾‾‾‾‾‾‾‾‾
ATCGAATATCAGTGATGAAAATAATAATAATAACGAATAAGCCAGAATCTTGCCATGAAGCCACAGTGGGA
TTCTGGGTTCCAATCAGAAATGGAGACAAGATAAAACTTGCATACATTCTTACCGATCACAGACGGGCCCCTGGTGTTTTGG
TAACTATTTACAAGGCATTTTTTACATATATTTGCACTTTTTATGTTTCTTTGGAAGACAAATGTATTTCAGAATA
   ‾‾‾‾‾‾‾‾‾
TATTTGTAGTCAATTCATATATATTTGAAGTGGAGCCATAGTAATGCCAGTAGATATCTCTATGATCTTGAGCTACTGGCAAC
 ‾‾‾‾‾‾‾‾‾‾‾                                                              (1699)
TTGTAAAGAAATATATATGACATATAAATGTATTGTAGCTTTCCGGTGTCAGCCACGGTGTATTTTCCACTTGGAATGAA
                                                                      ‾‾‾‾‾‾‾
ATTGTATCAACTGTGACATTATATGCCACTAGCAATAAAATGCTAATTGTTTCATGCTGTAAAAAAAAAAAAAAA
```

Fig. 1 (Continued)

A
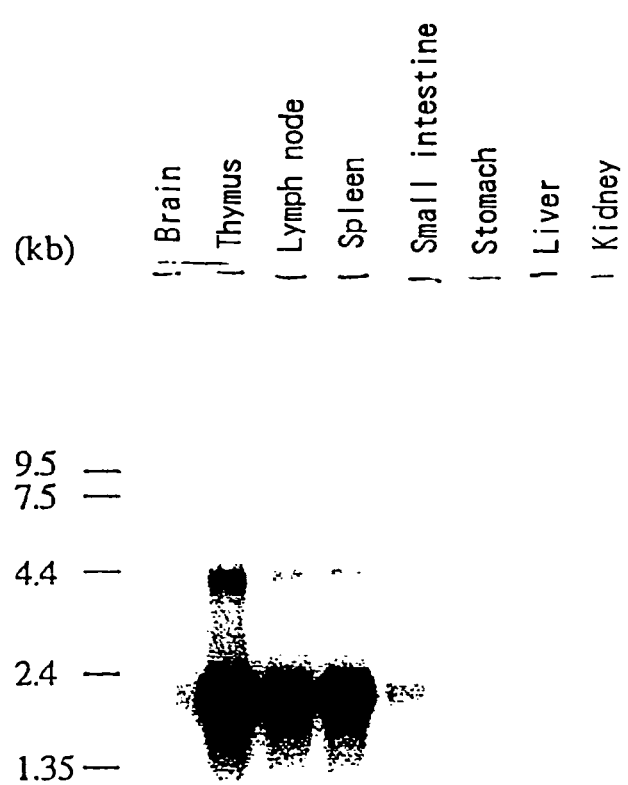
B
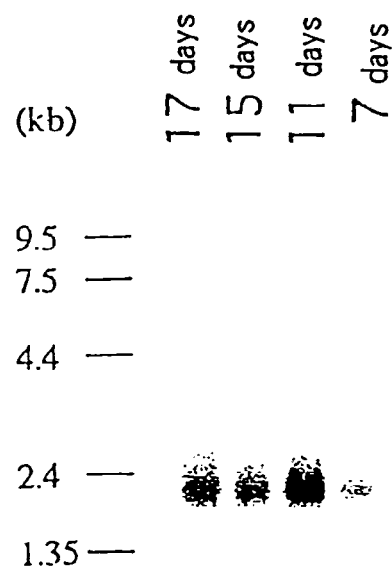
Fig. 2

SEQUENCE LISTING

<160> NUMBER OF SEQ ID NOS: 22

<210> SEQ ID NO 1
<211> LENGTH: 1877
<212> TYPE: DNA
<213> ORGANISM: Mus sp.
<220> FEATURE:
<221> NAME/KEY: CDS

<222> LOCATION: (120)..(1196)

<400> SEQUENCE: 1

```
ccatcctaat acgactcact atagggctcg agcggccgcc cgggcaggtg caggtagcag      60
tgaccctctg aggcgtttgg tgctccggta accaccacgg ctgtagagcg agtgttgcc     119
```

| | | | | | | | | | | | | | | | | |
|---|---|---|---|---|---|---|---|---|---|---|---|---|---|---|---|---|
| atg | gaa | ccg | atc | agt | gtg | agt | ata | tac | act | tct | gat | aac | tac | tct | gaa | 167 |
| Met | Glu | Pro | Ile | Ser | Val | Ser | Ile | Tyr | Thr | Ser | Asp | Asn | Tyr | Ser | Glu | |
| 1 | | | | 5 | | | | | 10 | | | | | 15 | | |
| gaa | gtg | ggg | tct | gga | gac | tat | gac | tcc | aac | aag | gaa | ccc | tgc | ttc | cgg | 215 |
| Glu | Val | Gly | Ser | Gly | Asp | Tyr | Asp | Ser | Asn | Lys | Glu | Pro | Cys | Phe | Arg | |
| | | | 20 | | | | | 25 | | | | | 30 | | | |
| gat | gaa | aac | gtc | cat | ttc | aat | agg | atc | ttc | ctg | ccc | acc | atc | tac | ttc | 263 |
| Asp | Glu | Asn | Val | His | Phe | Asn | Arg | Ile | Phe | Leu | Pro | Thr | Ile | Tyr | Phe | |
| | 35 | | | | | 40 | | | | | 45 | | | | | |
| atc | atc | ttc | ttg | act | ggc | ata | gtc | ggc | aat | gga | ttg | gtg | atc | ctg | gtc | 311 |
| Ile | Ile | Phe | Leu | Thr | Gly | Ile | Val | Gly | Asn | Gly | Leu | Val | Ile | Leu | Val | |
| 50 | | | | | 55 | | | | | 60 | | | | | | |
| atg | ggt | tac | cag | aag | aag | cta | agg | agc | atg | acg | gac | aag | tac | cgg | ctg | 359 |
| Met | Gly | Tyr | Gln | Lys | Lys | Leu | Arg | Ser | Met | Thr | Asp | Lys | Tyr | Arg | Leu | |
| 65 | | | | | 70 | | | | | 75 | | | | | 80 | |
| cac | ctg | tca | gtg | gct | gac | ctc | ctc | ttt | gtc | atc | aca | ctc | ccc | ttc | tgg | 407 |
| His | Leu | Ser | Val | Ala | Asp | Leu | Leu | Phe | Val | Ile | Thr | Leu | Pro | Phe | Trp | |
| | | | | 85 | | | | | 90 | | | | | 95 | | |
| gca | gtt | gat | gcc | atg | gct | gac | tgg | tac | ttt | ggg | aaa | ttt | ttg | tgt | aag | 455 |
| Ala | Val | Asp | Ala | Met | Ala | Asp | Trp | Tyr | Phe | Gly | Lys | Phe | Leu | Cys | Lys | |
| | | | 100 | | | | | 105 | | | | | 110 | | | |
| gct | gtc | cat | atc | atc | tac | act | gtc | aac | ctc | tac | agc | agc | gtt | ctc | atc | 503 |
| Ala | Val | His | Ile | Ile | Tyr | Thr | Val | Asn | Leu | Tyr | Ser | Ser | Val | Leu | Ile | |
| | 115 | | | | | 120 | | | | | 125 | | | | | |
| ctg | gcc | ttc | atc | agc | ctg | gac | cgg | tac | ctc | gcc | att | gtc | cac | gcc | acc | 551 |
| Leu | Ala | Phe | Ile | Ser | Leu | Asp | Arg | Tyr | Leu | Ala | Ile | Val | His | Ala | Thr | |
| 130 | | | | | 135 | | | | | 140 | | | | | | |
| aac | agt | caa | agg | cca | agg | aaa | ctg | ctg | gct | gaa | aag | gca | gtc | tat | gtg | 599 |
| Asn | Ser | Gln | Arg | Pro | Arg | Lys | Leu | Leu | Ala | Glu | Lys | Ala | Val | Tyr | Val | |
| 145 | | | | | 150 | | | | | 155 | | | | | 160 | |
| ggc | gtc | tgg | atc | cca | gcc | ctc | ctc | ctg | act | ata | cct | gac | ttc | atc | ttt | 647 |
| Gly | Val | Trp | Ile | Pro | Ala | Leu | Leu | Leu | Thr | Ile | Pro | Asp | Phe | Ile | Phe | |
| | | | | 165 | | | | | 170 | | | | | 175 | | |
| gcc | gac | gtc | agc | cag | ggg | gac | atc | agt | cag | ggg | gat | gac | agg | tac | atc | 695 |
| Ala | Asp | Val | Ser | Gln | Gly | Asp | Ile | Ser | Gln | Gly | Asp | Asp | Arg | Tyr | Ile | |
| | | | 180 | | | | | 185 | | | | | 190 | | | |
| tgt | gac | cgc | ctt | tac | ccc | gat | agc | ctg | tgg | atg | gtg | gtg | ttt | caa | ttc | 743 |
| Cys | Asp | Arg | Leu | Tyr | Pro | Asp | Ser | Leu | Trp | Met | Val | Val | Phe | Gln | Phe | |
| | | | | 195 | | | | | 200 | | | | | 205 | | |
| cag | cat | ata | atg | gtg | ggt | ctc | atc | ctg | ccc | ggc | atc | gtc | atc | ctc | tcc | 791 |
| Gln | His | Ile | Met | Val | Gly | Leu | Ile | Leu | Pro | Gly | Ile | Val | Ile | Leu | Ser | |
| 210 | | | | | 215 | | | | | 220 | | | | | | |
| tgt | tac | tgc | atc | atc | atc | tct | aag | ctg | tca | cac | tcc | aag | ggc | cac | cag | 839 |
| Cys | Tyr | Cys | Ile | Ile | Ile | Ser | Lys | Leu | Ser | His | Ser | Lys | Gly | His | Gln | |
| 225 | | | | | 230 | | | | | 235 | | | | | 240 | |
| aag | cgc | aag | gcc | ctc | aag | acg | aca | gtc | atc | ctc | atc | cta | gct | ttc | ttt | 887 |
| Lys | Arg | Lys | Ala | Leu | Lys | Thr | Thr | Val | Ile | Leu | Ile | Leu | Ala | Phe | Phe | |
| | | | | 245 | | | | | 250 | | | | | 255 | | |
| gcc | tgc | tgg | ctg | cca | tat | tat | gtg | ggg | atc | agc | atc | gac | tcc | ttc | atc | 935 |
| Ala | Cys | Trp | Leu | Pro | Tyr | Tyr | Val | Gly | Ile | Ser | Ile | Asp | Ser | Phe | Ile | |
| | | | 260 | | | | | 265 | | | | | 270 | | | |
| ctt | ttg | gga | gtc | atc | aag | caa | gga | tgt | gac | ttc | gag | agc | att | gtg | cac | 983 |
| Leu | Leu | Gly | Val | Ile | Lys | Gln | Gly | Cys | Asp | Phe | Glu | Ser | Ile | Val | His | |
| | | 275 | | | | | 280 | | | | | 285 | | | | |

-continued

```
aag tgg atc tcc atc aca gag gcc ctc gcc ttc ttc cac tgt tgc ctg      1031
Lys Trp Ile Ser Ile Thr Glu Ala Leu Ala Phe Phe His Cys Cys Leu
    290                 295                 300 aac ccc atc ctc tat gcc ttc ctc ggg gcc aag ttc aaa agc tct gcc      1079
Asn Pro Ile Leu Tyr Ala Phe Leu Gly Ala Lys Phe Lys Ser Ser Ala
305                 310                 315                 320 cag cat gca ctc aac tcc atg agc aga ggc tcc agc ctc aag atc ctt      1127
Gln His Ala Leu Asn Ser Met Ser Arg Gly Ser Ser Leu Lys Ile Leu
                325                 330                 335 tcc aaa gga aag cgg ggt gga cac tct tcc gtc tcc acg gag tca gaa      1175
Ser Lys Gly Lys Arg Gly Gly His Ser Ser Val Ser Thr Glu Ser Glu
            340                 345                 350 tcc tcc agt ttt cac tcc agc taacccttat gcaaagactt atataatata         1226
Ser Ser Ser Phe His Ser Ser
            355 tatatatata tgataaagaa cttttttatg ttacacattt tccagatata agagactgac    1286 cagtcttgta cagttttttt ttttttttaa ttgactgttg ggagtttatg ttcctctagt    1346 ttttgtgagg tttgacttaa tttatataaa tattgttttt tgtttgtttc atgtgaatga    1406 gcgtctaggc aggacctgtg gccaagttct tagtagctgt ttatctgtgt gtaggactgt    1466 agaactgtag aggaagaaac tgaacattcc agaatgtgtg gtaaattgaa taaagctagc    1526 cgtgatcctc agctgttgct gcataatctc ttcattccga ggagcacccc accccaccc    1586 ccaccccac cccattctta aattgtttgg ttatgctgtg tgatggtttg tttggttttt     1646 ttttgttgtt gttgttgttt ttttttttctg taaaagatgg cacttaaaac caaagcctga   1706 aatggtggta gaaatgctgg ggttttttttt gtttgtttgt tttttcagtt ttcaagagta   1766 gattgacttc agtccctaca aatgtacagt cttgtattac attgttaata aaagtcaatg    1826 ataaacttaa aaaaaaaaaa aaaaaaaaaa aaaaaaaaa aaaaaaaaaa a              1877
```

<210> SEQ ID NO 2
<211> LENGTH: 359
<212> TYPE: PRT
<213> ORGANISM: Mus sp.

<400> SEQUENCE: 2

```
Met Glu Pro Ile Ser Val Ser Ile Tyr Thr Ser Asp Asn Tyr Ser Glu
 1               5                  10                  15

Glu Val Gly Ser Gly Asp Tyr Asp Ser Asn Lys Glu Pro Cys Phe Arg
                20                  25                  30

Asp Glu Asn Val His Phe Asn Arg Ile Phe Leu Pro Thr Ile Tyr Phe
            35                  40                  45

Ile Ile Phe Leu Thr Gly Ile Val Gly Asn Gly Leu Val Ile Leu Val
        50                  55                  60

Met Gly Tyr Gln Lys Lys Leu Arg Ser Met Thr Asp Lys Tyr Arg Leu
65                  70                  75                  80

His Leu Ser Val Ala Asp Leu Leu Phe Val Ile Thr Leu Pro Phe Trp
                85                  90                  95

Ala Val Asp Ala Met Ala Asp Trp Tyr Phe Gly Lys Phe Leu Cys Lys
                100                 105                 110

Ala Val His Ile Ile Tyr Thr Val Asn Leu Tyr Ser Ser Val Leu Ile
            115                 120                 125

Leu Ala Phe Ile Ser Leu Asp Arg Tyr Leu Ala Ile Val His Ala Thr
        130                 135                 140

Asn Ser Gln Arg Pro Arg Lys Leu Leu Ala Glu Lys Ala Val Tyr Val
```

```
                145                 150                 155                 160
Gly Val Trp Ile Pro Ala Leu Leu Thr Ile Pro Asp Phe Ile Phe
                165                 170                 175

Ala Asp Val Ser Gln Gly Asp Ile Ser Gln Gly Asp Asp Arg Tyr Ile
                180                 185                 190

Cys Asp Arg Leu Tyr Pro Asp Ser Leu Trp Met Val Phe Gln Phe
                195                 200                 205

Gln His Ile Met Val Gly Leu Ile Leu Pro Gly Ile Val Ile Leu Ser
                210                 215                 220

Cys Tyr Cys Ile Ile Ile Ser Lys Leu Ser His Ser Lys Gly His Gln
225                 230                 235                 240

Lys Arg Lys Ala Leu Lys Thr Thr Val Ile Leu Ile Leu Ala Phe Phe
                245                 250                 255

Ala Cys Trp Leu Pro Tyr Tyr Val Gly Ile Ser Ile Asp Ser Phe Ile
                260                 265                 270

Leu Leu Gly Val Ile Lys Gln Gly Cys Asp Phe Glu Ser Ile Val His
                275                 280                 285

Lys Trp Ile Ser Ile Thr Glu Ala Leu Ala Phe Phe His Cys Cys Leu
                290                 295                 300

Asn Pro Ile Leu Tyr Ala Phe Leu Gly Ala Lys Phe Lys Ser Ser Ala
305                 310                 315                 320

Gln His Ala Leu Asn Ser Met Ser Arg Gly Ser Ser Leu Lys Ile Leu
                325                 330                 335

Ser Lys Gly Lys Arg Gly Gly His Ser Ser Val Ser Thr Glu Ser Glu
                340                 345                 350

Ser Ser Ser Phe His Ser Ser
            355

<210> SEQ ID NO 3
<211> LENGTH: 690
<212> TYPE: DNA
<213> ORGANISM: Mus sp.
<220> FEATURE:
<221> NAME/KEY: CDS
<222> LOCATION: (1)..(690)

<400> SEQUENCE: 3 ctg cac ctg tca gtg gct gac ctc ctc ttt gtc atc aca ctc ccc ttc       48
Leu His Leu Ser Val Ala Asp Leu Leu Phe Val Ile Thr Leu Pro Phe
  1               5                  10                  15 tgg gca gtt gat gcc atg gct gac tgg tac ttt ggg aaa ttt ttg tgt       96
Trp Ala Val Asp Ala Met Ala Asp Trp Tyr Phe Gly Lys Phe Leu Cys
             20                  25                  30 aag gct gtc cat atc atc tac act gtc aac ctc tac agc agc gtt ctc      144
Lys Ala Val His Ile Ile Tyr Thr Val Asn Leu Tyr Ser Ser Val Leu
         35                  40                  45 atc ctg gcc ttc atc agc ctg gac cgg tac ctc gcc att gtc cac gcc      192
Ile Leu Ala Phe Ile Ser Leu Asp Arg Tyr Leu Ala Ile Val His Ala
     50                  55                  60 acc aac agt caa agg cca agg aaa ctg ctg gct gaa aag gca gtc tat      240
Thr Asn Ser Gln Arg Pro Arg Lys Leu Leu Ala Glu Lys Ala Val Tyr
 65                  70                  75                  80 gtg ggc gtc tgg atc cca gcc ctc ctc ctg act ata cct gac ttc atc      288
Val Gly Val Trp Ile Pro Ala Leu Leu Leu Thr Ile Pro Asp Phe Ile
                     85                  90                  95 ttt gcc gac gtc agc cag ggg gac atc agt cag ggg gat gac agg tac      336
Phe Ala Asp Val Ser Gln Gly Asp Ile Ser Gln Gly Asp Asp Arg Tyr
                 100                 105                 110
```

```
atc tgt gac cgc ctt tac ccc gat agc ctg tgg atg gtg gtt ttt caa      384
Ile Cys Asp Arg Leu Tyr Pro Asp Ser Leu Trp Met Val Val Phe Gln
    115                 120                 125 ttc cag cat ata atg gtg ggt ctc atc ctg ccc ggc atc gtc atc ctc      432
Phe Gln His Ile Met Val Gly Leu Ile Leu Pro Gly Ile Val Ile Leu
130                 135                 140 tcc tgt tac tgc atc atc atc tct aag ctg tca cac tcc aag ggc cac      480
Ser Cys Tyr Cys Ile Ile Ile Ser Lys Leu Ser His Ser Lys Gly His
145                 150                 155                 160 cag aag cgc aag gcc ctc aag acg aca gtc atc ctc atc cta gct ttc      528
Gln Lys Arg Lys Ala Leu Lys Thr Thr Val Ile Leu Ile Leu Ala Phe
            165                 170                 175 ttt gcc tgc tgg ctg cca tat tat gtg ggg atc agc atc gac tcc ttc      576
Phe Ala Cys Trp Leu Pro Tyr Tyr Val Gly Ile Ser Ile Asp Ser Phe
                180                 185                 190 atc ctt ttg gga gtc atc aag caa gga tgt gac ttc gag agc att gtg      624
Ile Leu Leu Gly Val Ile Lys Gln Gly Cys Asp Phe Glu Ser Ile Val
            195                 200                 205 cac aag tgg atc tcc atc aca gag gcc ctc gcc ttc ttc cac tgt tgc      672
His Lys Trp Ile Ser Ile Thr Glu Ala Leu Ala Phe Phe His Cys Cys
    210                 215                 220 ctg aac ccc atc ctc tat                                               690
Leu Asn Pro Ile Leu Tyr
225                 230

<210> SEQ ID NO 4
<211> LENGTH: 230
<212> TYPE: PRT
<213> ORGANISM: Mus sp.

<400> SEQUENCE: 4

Leu His Leu Ser Val Ala Asp Leu Leu Phe Ile Thr Leu Pro Phe
 1               5                  10                  15

Trp Ala Val Asp Ala Met Ala Asp Trp Tyr Phe Gly Lys Phe Leu Cys
            20                  25                  30

Lys Ala Val His Ile Ile Tyr Thr Val Asn Leu Tyr Ser Ser Val Leu
        35                  40                  45

Ile Leu Ala Phe Ile Ser Leu Asp Arg Tyr Leu Ala Ile Val His Ala
    50                  55                  60

Thr Asn Ser Gln Arg Pro Arg Lys Leu Leu Ala Glu Lys Ala Val Tyr
65                  70                  75                  80

Val Gly Val Trp Ile Pro Ala Leu Leu Leu Thr Ile Pro Asp Phe Ile
                85                  90                  95

Phe Ala Asp Val Ser Gln Gly Asp Ile Ser Gln Gly Asp Asp Arg Tyr
            100                 105                 110

Ile Cys Asp Arg Leu Tyr Pro Asp Ser Leu Trp Met Val Val Phe Gln
        115                 120                 125

Phe Gln His Ile Met Val Gly Leu Ile Leu Pro Gly Ile Val Ile Leu
    130                 135                 140

Ser Cys Tyr Cys Ile Ile Ile Ser Lys Leu Ser His Ser Lys Gly His
145                 150                 155                 160

Gln Lys Arg Lys Ala Leu Lys Thr Thr Val Ile Leu Ile Leu Ala Phe
                165                 170                 175

Phe Ala Cys Trp Leu Pro Tyr Tyr Val Gly Ile Ser Ile Asp Ser Phe
            180                 185                 190

Ile Leu Leu Gly Val Ile Lys Gln Gly Cys Asp Phe Glu Ser Ile Val
        195                 200                 205
```

```
His Lys Trp Ile Ser Ile Thr Glu Ala Leu Ala Phe Phe His Cys Cys
    210                 215                 220

Leu Asn Pro Ile Leu Tyr
225                 230

<210> SEQ ID NO 5
<211> LENGTH: 685
<212> TYPE: DNA
<213> ORGANISM: Mus sp.
<220> FEATURE:
<221> NAME/KEY: CDS
<222> LOCATION: (120)..(683)

<400> SEQUENCE: 5
ccatcctaat acgactcact atagggctcg agcggccgcc cgggcaggtg caggtagcag      60
tgaccctctg aggcgtttgg tgctccggta accaccacgg ctgtagagcg agtgttgcc     119 atg gaa ccg atc agt gtg agt ata tac act tct gat aac tac tct gaa     167
Met Glu Pro Ile Ser Val Ser Ile Tyr Thr Ser Asp Asn Tyr Ser Glu
 1               5                  10                  15 gaa gtg ggg tct gga gac tat gac tcc aac aag gaa ccc tgc ttc cgg     215
Glu Val Gly Ser Gly Asp Tyr Asp Ser Asn Lys Glu Pro Cys Phe Arg
            20                  25                  30 gat gaa aac gtc cat ttc aat agg atc ttc ctg ccc acc atc tac ttc     263
Asp Glu Asn Val His Phe Asn Arg Ile Phe Leu Pro Thr Ile Tyr Phe
        35                  40                  45 atc atc ttc ttg act ggc ata gtc ggc aat gga ttg gtg atc ctg gtc     311
Ile Ile Phe Leu Thr Gly Ile Val Gly Asn Gly Leu Val Ile Leu Val
    50                  55                  60 atg ggt tac cag aag aag cta agg agc atg acg gac aag tac cgg ctg     359
Met Gly Tyr Gln Lys Lys Leu Arg Ser Met Thr Asp Lys Tyr Arg Leu
65                  70                  75                  80 cac ctg tca gtg gct gac ctc ctc ttt gtc atc aca ctc ccc ttc tgg     407
His Leu Ser Val Ala Asp Leu Leu Phe Val Ile Thr Leu Pro Phe Trp
                85                  90                  95 gca gtt gat gcc atg gct gac tgg tac ttt ggg aaa ttt ttg tgt aag     455
Ala Val Asp Ala Met Ala Asp Trp Tyr Phe Gly Lys Phe Leu Cys Lys
            100                 105                 110 gct gtc cat atc atc tac act gtc aac ctc tac agc agc gtt ctc atc     503
Ala Val His Ile Ile Tyr Thr Val Asn Leu Tyr Ser Ser Val Leu Ile
        115                 120                 125 ctg gcc ttc atc agc ctg gac cgg tac ctc gcc att gtc cac gcc acc     551
Leu Ala Phe Ile Ser Leu Asp Arg Tyr Leu Ala Ile Val His Ala Thr
    130                 135                 140 aac agt caa agg cca agg aaa ctg ctg gct gaa aag gca gtc tat gtg     599
Asn Ser Gln Arg Pro Arg Lys Leu Leu Ala Glu Lys Ala Val Tyr Val
145                 150                 155                 160 ggc gtc tgg atc cca gcc ctc ctc ctg act ata cct gac ttc atc ttt     647
Gly Val Trp Ile Pro Ala Leu Leu Leu Thr Ile Pro Asp Phe Ile Phe
                165                 170                 175 gcc gac gtc agc cag ggg gac atc agt cag ggg gat ga                  685
Ala Asp Val Ser Gln Gly Asp Ile Ser Gln Gly Asp
            180                 185

<210> SEQ ID NO 6
<211> LENGTH: 188
<212> TYPE: PRT
<213> ORGANISM: Mus sp.

<400> SEQUENCE: 6

Met Glu Pro Ile Ser Val Ser Ile Tyr Thr Ser Asp Asn Tyr Ser Glu
```

```
              1               5                  10                 15
            Glu Val Gly Ser Gly Asp Tyr Asp Ser Asn Lys Glu Pro Cys Phe Arg
                        20                  25                  30

Asp Glu Asn Val His Phe Asn Arg Ile Phe Leu Pro Thr Ile Tyr Phe
                        35                  40                  45

Ile Ile Phe Leu Thr Gly Ile Val Gly Asn Gly Leu Val Ile Leu Val
                        50                  55                  60

Met Gly Tyr Gln Lys Lys Leu Arg Ser Met Thr Asp Lys Tyr Arg Leu
             65                  70                  75                  80

His Leu Ser Val Ala Asp Leu Leu Phe Val Ile Thr Leu Pro Phe Trp
                        85                  90                  95

Ala Val Asp Ala Met Ala Asp Trp Tyr Phe Gly Lys Phe Leu Cys Lys
                       100                 105                 110

Ala Val His Ile Ile Tyr Thr Val Asn Leu Tyr Ser Ser Val Leu Ile
                       115                 120                 125

Leu Ala Phe Ile Ser Leu Asp Arg Tyr Leu Ala Ile Val His Ala Thr
                       130                 135                 140

Asn Ser Gln Arg Pro Arg Lys Leu Leu Ala Glu Lys Ala Val Tyr Val
            145                 150                 155                 160

Gly Val Trp Ile Pro Ala Leu Leu Leu Thr Ile Pro Asp Phe Ile Phe
                       165                 170                 175

Ala Asp Val Ser Gln Gly Asp Ile Ser Gln Gly Asp
                       180                 185

<210> SEQ ID NO 7
<211> LENGTH: 1694
<212> TYPE: DNA
<213> ORGANISM: Mus sp.
<220> FEATURE:
<221> NAME/KEY: CDS
<222> LOCATION: (1)..(1056)

<400> SEQUENCE: 7 ata tac act tct gat aac tac tct gaa gaa gtg ggg tct gga gac tat        48
Ile Tyr Thr Ser Asp Asn Tyr Ser Glu Glu Val Gly Ser Gly Asp Tyr
 1               5                  10                  15 gac tcc aac aag gaa ccc tgc ttc cgg gat gaa aac gtc cat ttc aat        96
Asp Ser Asn Lys Glu Pro Cys Phe Arg Asp Glu Asn Val His Phe Asn
                20                  25                  30 agg atc ttc ctg ccc acc atc tac ttc atc atc ttc ttg act ggc ata       144
Arg Ile Phe Leu Pro Thr Ile Tyr Phe Ile Ile Phe Leu Thr Gly Ile
            35                  40                  45 gtc ggc aat gga ttg gtg atc ctg gtc atg ggt tac cag aag aag cta       192
Val Gly Asn Gly Leu Val Ile Leu Val Met Gly Tyr Gln Lys Lys Leu
         50                  55                  60 agg agc atg acg gac aag tac cgg ctg cac ctg tca gtg gct gac ctc       240
Arg Ser Met Thr Asp Lys Tyr Arg Leu His Leu Ser Val Ala Asp Leu
 65                  70                  75                  80 ctc ttt gtc atc aca ctc ccc ttc tgg gca gtt gat gcc atg gct gac       288
Leu Phe Val Ile Thr Leu Pro Phe Trp Ala Val Asp Ala Met Ala Asp
                 85                  90                  95 tgg tac ttt ggg aaa ttt ttg tgt aag gct gtc cat atc atc tac act       336
Trp Tyr Phe Gly Lys Phe Leu Cys Lys Ala Val His Ile Ile Tyr Thr
            100                 105                 110 gtc aac ctc tac agc agc gtt ctc atc ctg gcc ttc atc agc ctg gac       384
Val Asn Leu Tyr Ser Ser Val Leu Ile Leu Ala Phe Ile Ser Leu Asp
         115                 120                 125 cgg tac ctc gcc att gtc cac gcc acc aac agt caa agg cca agg aaa       432
```

```
                Arg Tyr Leu Ala Ile Val His Ala Thr Asn Ser Gln Arg Pro Arg Lys
                        130                 135                 140 ctg ctg gct gaa aag gca gtc tat gtg ggc gtc tgg atc cca gcc ctc              480
Leu Leu Ala Glu Lys Ala Val Tyr Val Gly Val Trp Ile Pro Ala Leu
145                 150                 155                 160 ctc ctg act ata cct gac ttc atc ttt gcc gac gtc agc cag ggg gac              528
Leu Leu Thr Ile Pro Asp Phe Ile Phe Ala Asp Val Ser Gln Gly Asp
                165                 170                 175 atc agt cag ggg gat gac agg tac atc tgt gac cgc ctt tac ccc gat              576
Ile Ser Gln Gly Asp Asp Arg Tyr Ile Cys Asp Arg Leu Tyr Pro Asp
            180                 185                 190 agc ctg tgg atg gtg gtg ttt caa ttc cag cat ata atg gtg ggt ctc              624
Ser Leu Trp Met Val Val Phe Gln Phe Gln His Ile Met Val Gly Leu
        195                 200                 205 atc ctg ccc ggc atc gtc atc ctc tcc tgt tac tgc atc atc atc tct              672
Ile Leu Pro Gly Ile Val Ile Leu Ser Cys Tyr Cys Ile Ile Ile Ser
210                 215                 220 aag ctg tca cac tcc aag ggc cac cag aag cgc aag gcc ctc aag acg              720
Lys Leu Ser His Ser Lys Gly His Gln Lys Arg Lys Ala Leu Lys Thr
225                 230                 235                 240 aca gtc atc ctc atc cta gct ttc ttt gcc tgc tgg ctg cca tat tat              768
Thr Val Ile Leu Ile Leu Ala Phe Phe Ala Cys Trp Leu Pro Tyr Tyr
                245                 250                 255 gtg ggg atc agc atc gac tcc ttc atc ctt ttg gga gtc atc aag caa              816
Val Gly Ile Ser Ile Asp Ser Phe Ile Leu Leu Gly Val Ile Lys Gln
                260                 265                 270 gga tgt gac ttc gag agc att gtg cac aag tgg atc tcc atc aca gag              864
Gly Cys Asp Phe Glu Ser Ile Val His Lys Trp Ile Ser Ile Thr Glu
            275                 280                 285 gcc ctc gcc ttc ttc cac tgt tgc ctg aac ccc atc ctc tat gcc ttc              912
Ala Leu Ala Phe Phe His Cys Cys Leu Asn Pro Ile Leu Tyr Ala Phe
        290                 295                 300 ctc ggg gcc aag ttc aaa agc tct gcc cag cat gca ctc aac tcc atg              960
Leu Gly Ala Lys Phe Lys Ser Ser Ala Gln His Ala Leu Asn Ser Met
305                 310                 315                 320 agc aga ggc tcc agc ctc aag atc ctt tcc aaa gga aag cgg ggt gga             1008
Ser Arg Gly Ser Ser Leu Lys Ile Leu Ser Lys Gly Lys Arg Gly Gly
                325                 330                 335 cac tct tcc gtc tcc acg gag tca gaa tcc tcc agt ttt cac tcc agc             1056
His Ser Ser Val Ser Thr Glu Ser Glu Ser Ser Ser Phe His Ser Ser
                340                 345                 350 taaccccttat gcaaagactt atataatata tatatatata tgataaagaa cttttttatg          1116
ttacacattt tccagatata agagactgac cagtcttgta cagtttttt ttttttttaa            1176 ttgactgttg ggagtttatg ttcctctagt ttttgtgagg tttgacttaa tttatataaa          1236
tattgttttt tgtttgtttc atgtgaatga gcgtctaggc aggacctgtg gccaagttct          1296
tagtagctgt ttatctgtgt gtaggactgt agaactgtag aggaagaaac tgaacattcc          1356
agaatgtgtg gtaaattgaa taaagctagc cgtgatcctc agctgttgct gcataatctc          1416
ttcattccga ggagcacccc acccccaccc ccaccccac cccattctta aattgtttgg           1476
ttatgctgtg tgatggtttg tttggttttt ttttgttgtt gttgttgttt ttttttctg           1536 taaaagatgg cacttaaaac caaagcctga aatggtggta gaaatgctgg ggttttttt           1596 gtttgtttgt ttttcagtt ttcaagagta gattgacttc agtccctaca aatgtacagt           1656
cttgtattac attgttaata aaagtcaatg ataaactt                                   1694

<210> SEQ ID NO 8
```

-continued

```
<211> LENGTH: 352
<212> TYPE: PRT
<213> ORGANISM: Mus sp.

<400> SEQUENCE: 8

Ile Tyr Thr Ser Asp Asn Tyr Ser Glu Glu Val Gly Ser Gly Asp Tyr
  1               5                  10                  15

Asp Ser Asn Lys Glu Pro Cys Phe Arg Asp Glu Asn Val His Phe Asn
                 20                  25                  30

Arg Ile Phe Leu Pro Thr Ile Tyr Phe Ile Ile Phe Leu Thr Gly Ile
             35                  40                  45

Val Gly Asn Gly Leu Val Ile Leu Val Met Gly Tyr Gln Lys Lys Leu
 50                  55                  60

Arg Ser Met Thr Asp Lys Tyr Arg Leu His Leu Ser Val Ala Asp Leu
 65                  70                  75                  80

Leu Phe Val Ile Thr Leu Pro Phe Trp Ala Val Asp Ala Met Ala Asp
                 85                  90                  95

Trp Tyr Phe Gly Lys Phe Leu Cys Lys Ala Val His Ile Ile Tyr Thr
            100                 105                 110

Val Asn Leu Tyr Ser Ser Val Leu Ile Leu Ala Phe Ile Ser Leu Asp
            115                 120                 125

Arg Tyr Leu Ala Ile Val His Ala Thr Asn Ser Gln Arg Pro Arg Lys
130                 135                 140

Leu Leu Ala Glu Lys Ala Val Tyr Val Gly Val Trp Ile Pro Ala Leu
145                 150                 155                 160

Leu Leu Thr Ile Pro Asp Phe Ile Phe Ala Asp Val Ser Gln Gly Asp
                165                 170                 175

Ile Ser Gln Gly Asp Asp Arg Tyr Ile Cys Asp Arg Leu Tyr Pro Asp
            180                 185                 190

Ser Leu Trp Met Val Val Phe Gln Phe Gln His Ile Met Val Gly Leu
            195                 200                 205

Ile Leu Pro Gly Ile Val Ile Leu Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Val Gly Ile Ser Ile Asp Ser Phe Ile Leu Leu Gly Val Ile Lys Gln
            260                 265                 270

Gly Cys Asp Phe Glu Ser Ile Val His Lys Trp Ile Ser Ile Thr Glu
            275                 280                 285

Ala Leu Ala Phe Phe His Cys Cys Leu Asn Pro Ile Leu Tyr Ala Phe
            290                 295                 300

Leu Gly Ala Lys Phe Lys Ser Ser Ala Gln His Ala Leu Asn Ser Met
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
            DNA
<220> FEATURE:
<221> NAME/KEY: modified_base
<222> LOCATION: (13)
<223> OTHER INFORMATION: i
<220> FEATURE:
<221> NAME/KEY: modified_base
<222> LOCATION: (15)
<223> OTHER INFORMATION: i

<400> SEQUENCE: 9
ctsmgtttgk cmntnkcyga                                       20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: modified_base
<222> LOCATION: (8)..(9)
<223> OTHER INFORMATION: i
<220> FEATURE:
<221> NAME/KEY: modified_base
<222> LOCATION: (17)
<223> OTHER INFORMATION: i

<400> SEQUENCE: 10
tagaksanng grttsanrca rcagtg                                26

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
tcatccccct gactgatgtc cccct                                 25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ccatcctaat acgactcact atagggc                               27

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
cgcgtcgacc acaacatgct gtccacatca                            30

<210> SEQ ID NO 14
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 14
cgctctagat tataaaccag ccgagacttc                                         30

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
cgcgtcgacg ttaccatgga ggggatcag                                          29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
cgcgcggccg cttagctgga gtgaaaactt ga                                      32

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tagcggccgc gttgccatgg aaccgat                                            27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gcgtcgacta agggttagct ggagtga                                            27

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
ctgcacctgt cagtggctga                                                    20

<210> SEQ ID NO 20
<211> LENGTH: 27
<212> TYPE: DNA
<213> ORGANISM: Artificial Sequence
<220> FEATURE:
```

<223> OTHER INFORMATION: Description of Artificial Sequence: Synthetic
DNA

<400> SEQUENCE: 20
tagatgaggg ggattgagac aacagtg                                                27

<210> SEQ ID NO 21
<211> LENGTH: 1776
<212> TYPE: DNA
<213> ORGANISM: Mus musculus
<220> FEATURE:
<221> NAME/KEY: CDS
<222> LOCATION: (59)..(325)

<400> SEQUENCE: 21

```
ctcggtgtcc tcttgctgtc cagctctgca gcctccggcg cgccctcccg cccacgcc            58 atg gac gcc aag gtc gtc gcc gtg ctg gcc ctg gtg ctg gcc gcg ctc          106
Met Asp Ala Lys Val Val Ala Val Leu Ala Leu Val Leu Ala Ala Leu
 1               5                   10                  15 tgc atc agt gac ggt aaa cca gtc agc ctg agc tac cga tgc ccc tgc          154
Cys Ile Ser Asp Gly Lys Pro Val Ser Leu Ser Tyr Arg Cys Pro Cys
             20                  25                  30 cgg ttc ttc gag agc cac atc gcc aga gcc aac gtc aag cat ctg aaa          202
Arg Phe Phe Glu Ser His Ile Ala Arg Ala Asn Val Lys His Leu Lys
         35                  40                  45 atc ctc aac act cca aac tgt gcc ctt cag att gtt gca cgg ctg aag          250
Ile Leu Asn Thr Pro Asn Cys Ala Leu Gln Ile Val Ala Arg Leu Lys
     50                  55                  60 aac aac aac aga caa gtg tgc att gac ccg aaa tta aag tgg atc caa          298
Asn Asn Asn Arg Gln Val Cys Ile Asp Pro Lys Leu Lys Trp Ile Gln
 65                  70                  75                  80 gag tac ctg gag aaa gct tta aac aag taagcacaac agcccaaagg                 345
Glu Tyr Leu Glu Lys Ala Leu Asn Lys
                 85 actttccagt agaccccga ggaaggctga catccgtggg agatgcaagg gcagtggtgg          405 ggaggagggc ctgaaccctg ccaggatggc cggcgggac agcactgact ggggtcatgc          465 taaggtttgc cagcataaag acactccgcc atagcatatg gtacgatatt gcagcttata        525 ttcatccctg ccctcgcccg tgcacaatgg agcttttata actggggttt ttctaaggaa        585 ttgtattacc ctaaccagtt agcttcatcc ccattctcct catcctcatc ttcattttaa        645 aaagcagtga ttacttcaag ggctgtattc agtttgcttt ggagcttctc tttgccctgg        705 ggcctctggg cacagttata gacggtggct ttgcaggggaa ccctagagag aaaccttcca        765 ccagagcaga gtccgaggaa cgctgcaggg cttgtcctgc aggggcgct cctcgacaga         825 tgccttgtcc tgagtcaaca caagatccgg cagagggagg ctcctttatc cagttcagtg        885 ccagggtcgg gaagcttcct ttagaagtga tccctgaagc tgtgctcaga gacccttcc         945 tagccgttcc tgctctctgc ttgcctccaa acgcatgctt catctgactt ccgcttctca       1005 cctctgtagc ctgacggacc aatgctgcaa tggaagggag gagagtgatg tggggtgccc       1065 cctccctctc ttcccttttgc tttcctctca cttgggccct ttgtgagatt tttctttggc     1125 ctcctgtaga atggagccag accatcctgg ataatgtgag aacatgccta gatttaccca       1185 caaaacacaa gtctgagaat taatcataaa cggaagttta atgaggatt tggacttttgg       1245 taattgtccc tgagtcctat atattcaac agtggctcta tgggctctga tcgaatatca        1305 gtgatgaaaa taataataat aataataata acgaataagc cagaatcttg ccatgaagcc       1365 acagtgggga ttctgggttc caatcagaaa tggagacaag ataaaacttg catacattct      1425
```

```
tacgatcaca gacggccctg gtggtttttg gtaactattt acaaggcatt tttttacata  1485 tattttgtg  cacttttat  gtttctttgg aagacaaatg tatttcagaa tatatttgta  1545
gtcaattcat atatttgaag tggagccata gtaatgccag tagatatctc tatgatcttg  1605
agctactggc aacttgtaaa gaaatatata tgacatataa atgtattgta gctttccggt  1665
gtcagccacg gtgtattttt ccacttggaa tgaaattgta tcaactgtga cattatatgc  1725
actagcaata aaatgctaat tgtttcatgc tgtaaaaaaa aaaaaaaaaa a            1776
```

<210> SEQ ID NO 22
<211> LENGTH: 89
<212> TYPE: PRT
<213> ORGANISM: Mus musculus

<400> SEQUENCE: 22

```
Met Asp Ala Lys Val Val Ala Val Leu Ala Leu Val Leu Ala Ala Leu
 1               5                  10                  15

Cys Ile Ser Asp Gly Lys Pro Val Ser Leu Ser Tyr Arg Cys Pro Cys
                20                  25                  30

Arg Phe Phe Glu Ser His Ile Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85
```

MOUSE CXC CHEMOKINE RECEPTOR

CROSS REFERENCE TO RELATED APPLICATIONS

The present application is a 37 C.F.R. § 1.53(b) divisional of U.S. application Ser. No. 09/367,052 filed Aug. 6, 1999, now U.S. Pat. No. 7,074,616 which is the National Phase of International Application No. PCT/JP97/00299 filed Feb. 7, 1997. Each of these applications are hereby incorporated by reference.

1. Technical Field

The present invention relates to a novel murine CXC chemokine receptor, and a murine chemokine receptor gene. More particularly, it relates to a polypeptide encoded by the gene, an expression vector carrying the gene, a transformant into which the expression vector is introduced, and a monoclonal antibody against the polypeptide. Further, it relates to a method for producing the polypeptide using the transformant. Furthermore, it relates to a method of screening an agonist or antagonist of chemokines, and a method of screening an AIDS onset inhibitor or an HIV-1 infection inhibitor.

2. Background Art

When a tissue impairment takes place owing to causation such as a bacterial or viral infection, a physical or chemical trauma, an autoimmune disease, an allergic disease or the like, an inflammatory reaction accompanied with signs such as flare, edema, fever and pain is induced, and accumulation and infiltration of peripheral leukocytes are observed at the local inflammation. The kinds of the leukocytes infiltrating on the site of an inflammation vary depending on the diseases. An acute inflammation such as an ordinary bacterial infection, an immunological complex deposition and a trauma involves accumulation and infiltration mainly of a neutrophile; a tubercular infection, a typhoid infection and a delayed hypersensitivity involve those mainly of a monocyte; and a viral infection involves those mainly of a lymphocyte, while an eosinophile and a basophile infiltrate accompanied with an immediate allergy and a parasite infection [Baggioloni, M. et al., *Immunol. Today*, 15, 127-133 (1994)]. Recently, there have been found that chemotactic factors of polypeptides having certain degrees of selectivity to leukocytes having chemotactic activities, the polypeptides having characteristic four cysteine residues. Since they are in a family, members of which are homologous in their amino acid sequences and related to each other also in terms of the biological activities, they are referred to as chemokines (having chemoattractant and cytokine activity) [Lindley, I. J. D. et al., *Immunol. Today*, 14-24 (1993)].

Four cysteine residues of a chemokine are linked with disulfide bonds between the first and third residues and between the second and fourth residues, respectively. Since their characteristics are found on the biological activities in which whether or not one additional amino acid is contained between the first and second cysteine residues, their subfamilies are distinguished by referring to as CXC chemokines and CC chemokines [Baggioloni, M. et al., *Adv. Immunol.*, 55, 97-179 (1994)].

The CXC chemokines which have been found so far are PBSF/SDF-1; IL-8 [Yoshimura, T. et al., *Proc. Natl. Acad. Sci. U.S.A.*, 84, 9233-9237 (1987)]; NAP-2 [Walz, A. et al., *Biochem. Biophys. Res. Commun.*, 159, 969-975 (1989)]; NAP-4; GROα [Richmondo, A. et al., *J Cell. Biochem.*, 36, 185-198 (1988)]; GROβ [Haskill, S. et al., *Proc. Natl. Acad. Sci. U.S.A.*, 87, 77732-7736 (1990)]; GROγ [Haskill, S. et al., (1990) ibid]; GCP-2 [Proos t, P. et al., *J Immunol.*, 150, 1000-1010 (1993)]; ENA-78 [Wayz, A. et al., *J Exp. Med.*, 174, 1355-1362 (1991)]; PF-4 [Deuel, T. F. et al., *Proc. Natl. Acad. Sci. U.S.A.*, 74, 2256-2258 (1977)]; a human CXCR4/fusin/HUMSTSR [Feng, Y. et al., *Science*, 272, 872-877 (1996)]; and IP-10 [Dewald, B. et al., *Immunol. Lett.*, 32, 81-84 (1992)].

And the CC chemokines are MCP-1 [Yoshimura, T. et al., *J Immunol.*, 142, 1956-1962 (1989)]; MCP-2 [Chang, H. C. et al., *Int. Immunol.*, 1, 388-397 (1989)]; MCP-3 [Van Damme, J. et al., *J Exp. Med*, 176, 59-65 (1992)]; MIP-1α [Obaku, K. et al., *J Biochem.*, 99, 885-894 (1986)]; MIP-1β [Lipes, M. A. et al., *Proc. Natl. Acad. Sci. U.S.A.*, 85, 9704-9708 (1988)]; RANTES [Schall, T. et al., *J Immunol.*, 141, 1018-1025 (1988)]; I-309 [Miller, M. D. et al., *J Immunol.*, 143, 2907-2916 (1989)]; and eotaxin [Jose, P. et al., *J Exp. Med*, 179, 881-887 (1994)].

Most of the CXC chemokines have chemotactic activities on a neutrophile but not on a monocyte. Most of the CC chemokines have chemotactic activities on a monocyte but not on a neutrophile. In addition, as to other leukocytes such as an eosinophile, a basophile and a lymphocyte, there have been reported to have the chemotactic activities for some of CXC and CC chemokines. While CC chemokines including RANTES, MIP-1α and MCP-1, and IL-8, which is a CXC chemokine, have been found to possess chemotactic activities on human lymphocytes, none of them are chemotactic factors specific to lymphocytes.

It has been reported that murine PBSF/SDF-1 is a CXC chemokine which is identified as a murine pre-B-cell growth-stimulating factor originally secreted from a murine bone marrow stromal cell line PA6 with its amino acid sequence (FIG. 1) (SEQ ID NO:22) [Nagasawa, T. et al., *Proc. Natl. Acad. Sci. USA*, 91, 2305-2309 (1994)]. In addition, recently, it has been clarified to have a potent chemotactic activity also on a human T lymphocyte [Bleul, C. et al., *J Exp. Med.*, 184, 1101-1110].

Various studies have been conducted on receptors for chemokines. There have been reported IL-8RA, which is a receptor specific to IL-8; IL-8RB, which is a receptor for IL-8 and other CXC chemokines; CC CKR1, which is a receptor specific to MIP-1α and RANTES; CC CKR2A, which is a receptor specific to MCP-1; CC CKR2B, which is a receptor specific to MCP-1 and MCP-3; CC CKR3, which is a receptor specific to eotaxin, MCP-3, and RANTES [Combadiere, C. et al., *J Biol.*, 270, 16491-16494 (1995)]; and CC CKR5, which is a receptor specific to MIP-1α, MIP-1β and RANTES. Recently, CXCR4/fusin/HUMSTSR has been identified as a receptor for SDF-1 which is a human CXC chemokine.

In addition, among the chemokine receptors mentioned above, there has been clarified that CC CKR5, CC CKR2B, CC CKR3 and CXCR4/fusin/HUMSTSR have functions as receptors for HIV-1 by acting cooperatively with CD4, a protein present on a cell membrane, and that an infection with HIV-1 mediated by each receptor is inhibited by the ligands of these receptors.

Two characteristically different HIV-1s are involved in the infection with an HIV-1, which is an AIDS-causing virus, and in the onset of AIDS. A monocyte-tropic HIV-1 with which monocytes, macrophages and T lymphocytes are mainly infected is involved in the viral proliferation in a human body during the period of infection and latent infection, and a T-cell-line-tropic HIV-1 with which T lymphocytes are mainly infected is involved in the reduction of the number of T lymphocytes and the onset of AIDS. In order to infect cells with the two HIV-1s mentioned above, two receptors are required. One is CD4 protein, which is a cell membrane protein, and is a common receptor for the two HIV-1s mentioned above. The other is a protein referred to as a coreceptor which has an activity as a receptor by acting cooperatively with the CD4 protein, and is specific to each of the two HIV-1s.

Recently, there has been clarified that a coreceptor for a main monocyte-tropic HIV-1 is found to be CC CKR5, which is a CC chemokine receptor, and a coreceptor for T-cell-line-tropic HIV-1 is found to be human CXCR4/fusin/ HUMSTSR, which is a CXC chemokine receptor. Further, there has been clarified that the infection with a monocyte-tropic HIV-1 is inhibited by MIP-1α, MIP-1β and RANTES, which are CC CKR5 ligands, and the infection with a T-cell-tropic HIV-1 is inhibited by a human PBSF/SDF-1, which is a human CXCR4/fusin/HUMSTSR ligand, suggesting that the chemokine receptors described above could be a target of an HIV-1 infection inhibitor.

On the other hand, which domain in a human CXCR4/ fusin/HUMSTSR is essential for the infection with a T-cell-line-tropic HIV-1 has not been identified so far. A CXC chemokine receptor, human CXCR4/fusin/HUMSTSR is a seven transmembrane-spanning-domain receptor, and a three-dimensional structure formed by four extracellular domains is considered to be significant in the binding with a ligand or an HIV-1. For the purpose of identifying a functional domain of a human CXCR4/fusin/HUMSTSR, it is necessary to produce a CXCR4/fusin/HUMSTSR variant so as to maintain the three-dimensional structure as a receptor. The identification of a functional domain of a human CXCR4/fusin/HUMSTSR is extremely useful in the development of an HIV-1 infection inhibitor.

In addition, the elucidation of the mechanism for causation of an HIV-1 species-specificity is significant in the development of an HIV-1 infection model animal, as in the case of clarifying an intracellular factor required for a viral infection. Although a mouse is an excellent experimental animal which can easily be handled and obtained at a low cost of which characteristics are clarified in detail, there has been no report that a mouse is infected with an HIV-1.

Murine cells have several barriers concerning an HIV-1 viral infection. A first barrier is present on the stage where a virus is bound to murine cells. A human CD4 is bound to an HIV-1, but a murine CD4 is not bound to an HIV-1. However, there has been clarified in the existing studies that when a human CD4 is expressed in vitro on the surface of murine cell lines including a T-cell line, the adsorption of an HIV to the cells takes place, but an entry into the cells does not. It was clarified from the above results that the murine cells expressing a human CD4 do not support an entry of the virus, suggesting that there is a receptor, in addition to CD4, which is human-specific and essential for a membrane fusion (which takes place at an entry of the virus) of which molecule is absent in murine cells.

The HIV-1 is recognized to have a difference in an infection ability to CD 4-positive cells depending on the strains. Some strains are classified as monocyte- or macrophage-tropic (M-tropic) strains since they infect a monocyte, and others are classified as T-cell-line-tropic (T-tropic) strains since they infect a T-cell line.

As an HIV-1 infection is progressed, a monocyte-tropic virus observed frequently at an initial stage of the infection is replaced with a T-cell-line-tropic virus. In 1996, there has been reported that CXCR4/fusin, which is a seven transmembrane-spanning-domain G protein-coupled receptor, is essential for the entry of a T-cell-line-tropic HIV-1 into human CD4-positive cells. These results urged the present inventors to study whether or not the function of the CXCR4 as a viral entry receptor is species-specific.

DISCLOSURE OF THE INVENTION

The present inventors have clarified that a murine CXCR4 as a receptor of a murine PBSF/SDF-1, which is one of CXC chemokines, is isolated, and found its amino acid sequence to be in 90% identity with a human CXCR4. The present inventors have established cells transfected with a human CD4 and a murine CXCR4, and studied whether or not a human CXCR4, which is an HIV-1 receptor, serves as a barrier against an HIV-1 entry present in the murine cells.

Accordingly, an object of the present invention is to provide a novel murine CXC chemokine receptor gene; a polypeptide encoded by the gene; an expression vector carrying the gene; a transformant harboring the expression vector; a monoclonal antibody against the polypeptide; a method for producing the polypeptide; and a method of screening an agonist or antagonist of the polypeptide and also a method of screening an HIV-1 infection inhibitor, each of which is useful in studies of a therapeutic agent for AIDS and the functional mechanism of HIV-1 infection.

Specifically, as a result of intensive studies in order to solve the problems described above, the present inventors have succeeded in cloning a novel murine chemokine receptor gene from a murine pre-B-cell line DW34 of which growth is enhanced depending on a murine PBSF/SDF-1. The present inventors have also found that cells expressing murine CXCR4 and human CD4 fuse with cells expressing an env protein derived from a T-cell-line-tropic HIV-1 strain, and those cells are infected with such a T-cell-line-tropic HIV-1 strain. These results lead to a conclusion that CXCR4 is not a species-specific barrier against the entry of a T-cell-line-tropic HIV-1, which is present in the murine cells. In addition, because of the fact that a T-cell-line-tropic HIV-1 chimera virus clone of which env or V3 region is replaced with that of a monocyte-tropic HIV-1 does not infect cells expressing murine CXCR4 and human CD4 cells, there has been revealed that a V3 loop of an HIV-1 envelope protein is essential for a murine CXCR4-mediated HIV-1 entry. Based on these findings, the present invention has been completed.

In sum, the present invention pertains to:

(1) a DNA encoding a polypeptide comprising an entire sequence of the amino acid sequence as shown by SEQ ID NO: 2 or a partial sequence thereof, or a polypeptide comprising the polypeptide described above, wherein any of the polypeptides has an activity of a receptor capable of binding to a murine PBSF/SDF-1;

(2) a DNA encoding a polypeptide resulting from at least one of deletion, addition, insertion, or substitution of one or more amino acid residues in an entire sequence of the amino acid sequence as shown by SEQ ID NO: 2 or a partial sequence thereof, wherein any of the polypeptides has an activity of a receptor capable of binding to a murine PBSF/SDF-1;

(3) a DNA comprising an entire sequence of the nucleotide sequence as shown by SEQ ID NO: 1 or a partial sequence thereof, or a DNA comprising the DNA described above, wherein any of the DNAs encodes a polypeptide having an activity of a receptor capable of binding to a murine PBSF/SDF-1;

(4) a DNA resulting from at least one of deletion, addition, insertion, or substitution of one or more bases in a DNA comprising an entire sequence of the nucleotide sequence as shown by SEQ ID NO: 1 or a partial sequence thereof, or a DNA comprising the DNA, wherein any of the DNAs encodes a polypeptide having an activity of a receptor capable of binding to a murine PBSF/SDF-1;

(5) a DNA being capable of hybridizing under stringent conditions with the DNA of any one of items (1) to (4) above, and encoding a polypeptide having an activity of a receptor capable of binding to a murine PBSF/SDF-1;

(6) a polypeptide encoded by the DNA of any one of items (1) to (5) above, wherein the polypeptide has an activity of a receptor capable of binding to a murine PBSF/SDF-1;

(7) a polypeptide comprising an entire amino acid sequence as shown by SEQ ID NO: 2 or a partial sequence thereof, or a polypeptide comprising the polypeptide described above, wherein any of the polypeptides has an activity of a receptor capable of binding to a murine PBSF/SDF-1;

(8) a polypeptide resulting from at least one of deletion, addition, insertion, or substitution of one or more amino acid residues in an entire amino acid sequence as shown by SEQ ID NO: 2 or a partial sequence thereof, wherein the polypeptide has an activity of a receptor capable of binding to a murine PBSF/SDF-1;

(9) the polypeptide according to any one of items (6) to (8) above, derived from a murine pre-B-cell line DW34;

(10) an expression vector carrying the DNA according to any one of items (1) to (5) above;

(11) a transformant obtained by introducing the expression vector according to item (10) above into a host;

(12) the transformant according to item (11) above, wherein the host is a mammalian cell line;

(13) a method for producing a polypeptide having an activity of a receptor capable of binding to a murine PBSF/SDF-1, characterized in that the method comprises culturing the transformant according to item (11) or (12) above under conditions capable of expressing the expression vector according to item (10) above;

(14) a monoclonal antibody against the polypeptide according to any one of items (6) to (9) above;

(15) a pharmaceutical composition for the use as an AIDS onset inhibitor or an HIV-1 infection inhibitor, comprising a murine PBSF/SDF-1;

(16) cells expressing the polypeptide according to any one of items (6) to (9) above and a human CD4 protein;

(17) a method of screening an AIDS onset inhibitor or an HIV-1 infection inhibitor, characterized in that the method comprises the steps of:
(a) mixing the cells expressing the polypeptide according to any one of items (6) to (9) above, or cells according to item (16) above; a human T-cell-line-tropic HIV-1; and a substance to be screened, and incubating the resulting mixture; and
(b) analyzing localization of an HIV-1 in the cells;

(18) the method according to item (17) above, wherein the step of analyzing localization of an HIV-1 is carried out by using a monoclonal antibody against a human T-cell-line-tropic HIV-1;

(19) a method of screening an AIDS onset inhibitor or an HIV-1 infection inhibitor, characterized in that the method comprises the steps of:
(a) mixing the cells expressing the polypeptide according to any one of items (6) to (9) above, or cells according to item [16] above; cells expressing an HIV-1 envelope protein; and a substance to be screened, and incubating the resulting mixture; and
(b) determining a level of the fusion of the above cells with the cells expressing an HIV-1 envelope protein;

(20) a method of screening an AIDS onset inhibitor or an HIV-1 infection inhibitor, or a PBSF/SDF-1 agonist or antagonist, characterized in that the method comprises the steps of:
(a) mixing the cells expressing the polypeptide according to any one of items (6) to (9) above, or cells according to item (16) above; a murine or human PBSF/SDF-1; and a substance to be screened, and incubating the resulting mixture; and
(b) determining an intracellular calcium ion level and/or determining a binding activity of an expressed polypeptide with the murine or human PBSF/SDF-1;

(21) the method according to item (20) above, wherein the antagonist is a hematopoetic stem cell liberator;

(22) a kit for detecting an AIDS onset or an HIV-1 infection, comprising the cells expressing the polypeptide according to any one of items items (6) to (9) above, or cells according to item (16) above; and

(23) a method for detecting an AIDS onset or an HIV-1 infection, characterized in that the method comprises;
(a) mixing the cells expressing the polypeptide according to any one of items items (6) to (9) above, or cells according to item (16) above with sera, blood cells or blood of a patient suspected to be infected with an HIV-1, and incubating the resulting mixture, and
(b) analyzing localization of an HIV-1 in the cells or determining a level of the fusion of the cells with HIV-1-infected cells.

BRIEF DESCRIPTION OF THE DRAWINGS

FIG. 1 shows a nucleotide sequence of a murine PBSF/SDF-1 cDNA (SEQ ID NO: 21), and an amino acid sequence (SEQ ID NO: 22) of a murine PBSF/SDF-1 encoded by the above nucleotide sequence.

FIG. 2 shows electrophoretic results of Example 2 by means of Northern blotting method, wherein A shows the results on mRNA of murine tissues; and B shows the results on mRNA of murine fetus.

BEST MODE FOR CARRYING OUT THE INVENTION

DNA of the Present Invention

Figure 3:
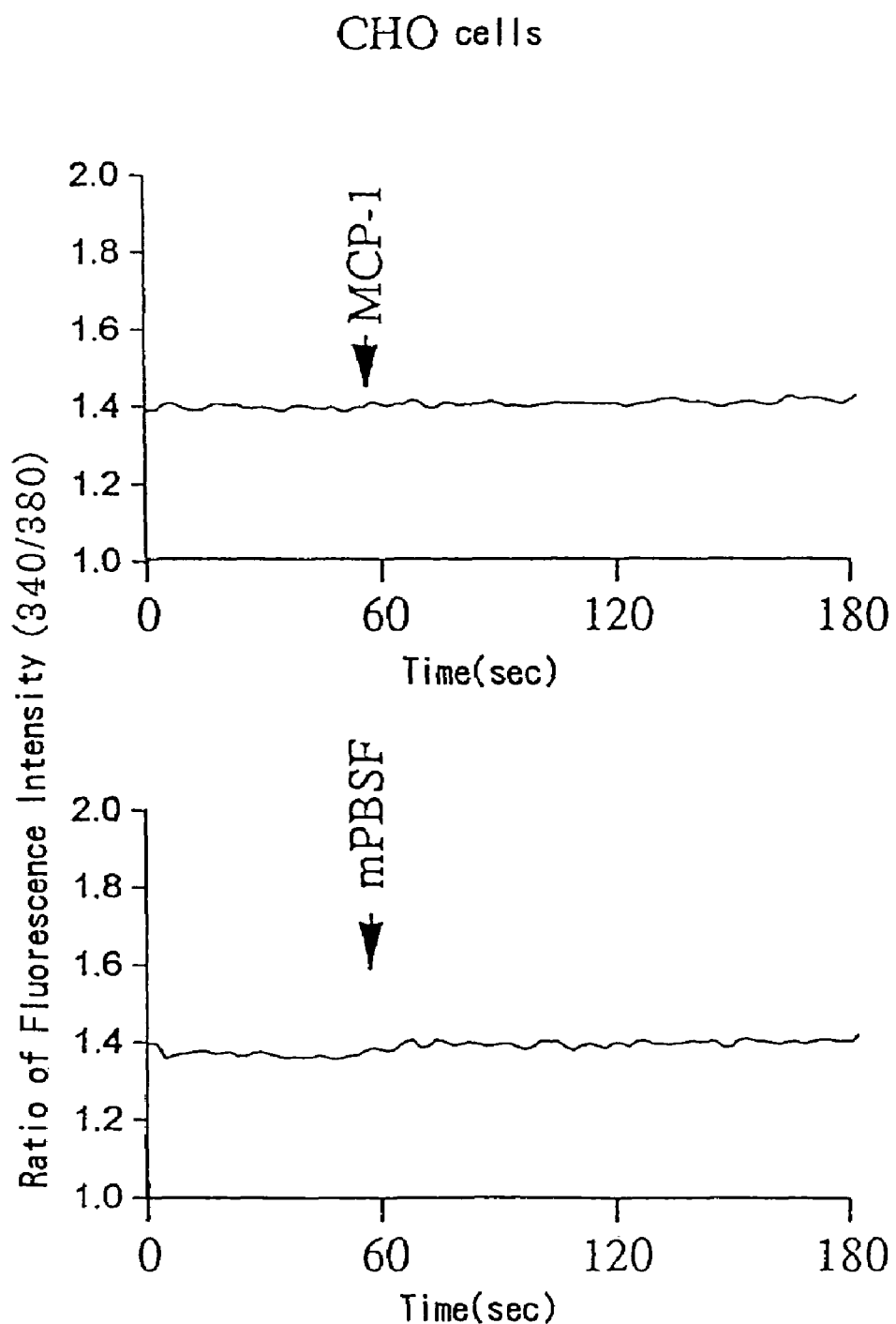
FIG. 3 is graphs each showing results of Example 6, wherein the abscissa indicates the passage of period of time, and the ordinate indicates the ratio of fluorescence intensities ([fluorescence intensity at 340 nm]/[fluorescence intensity at 380 nm]). The cells used are CHO cells in which the chemokine receptor is not expressed.
Figure 4:
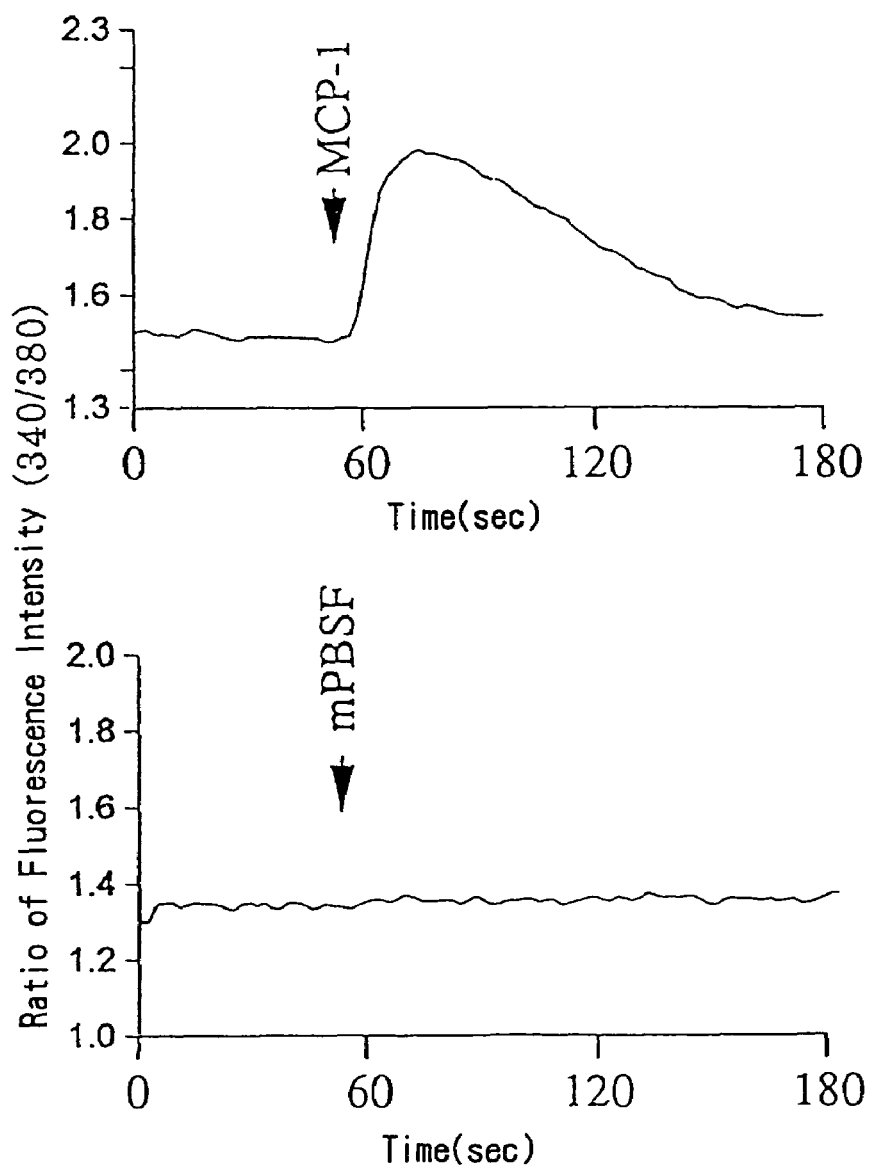
FIG. 4 is graphs each showing results of Example 6, wherein the abscissa indicates the passage of period of time, and the ordinate indicates the ratio of fluorescence intensities ([fluorescence intensity at 340 nm]/[fluorescence intensity at 380 nm]). The cells used are CHO cells in which the human chemokine receptor CC CKR2B is expressed.
Figure 5:
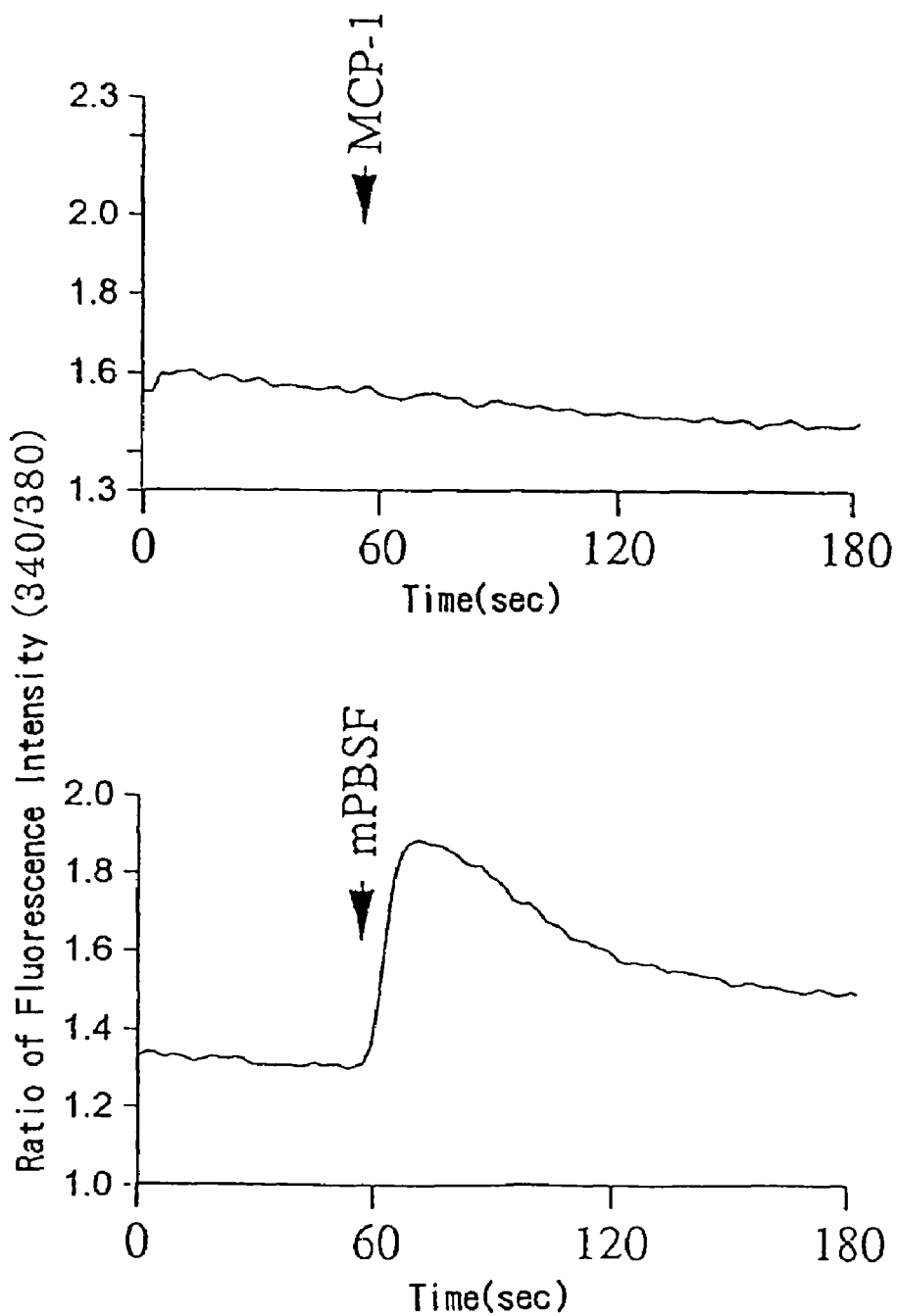
FIG. 5 is graphs each showing results of Example 6, wherein the abscissa indicates the passage of period of time, and the ordinate indicates the ratio of fluorescence intensities ([fluorescence intensity at 340 nm]/[fluorescence intensity at 380 nm]). The cells used are CHO cells in which the receptor (murine CXCR4) of murine chemokine (PBSF/SDF-1) is expressed.
Figure 6:
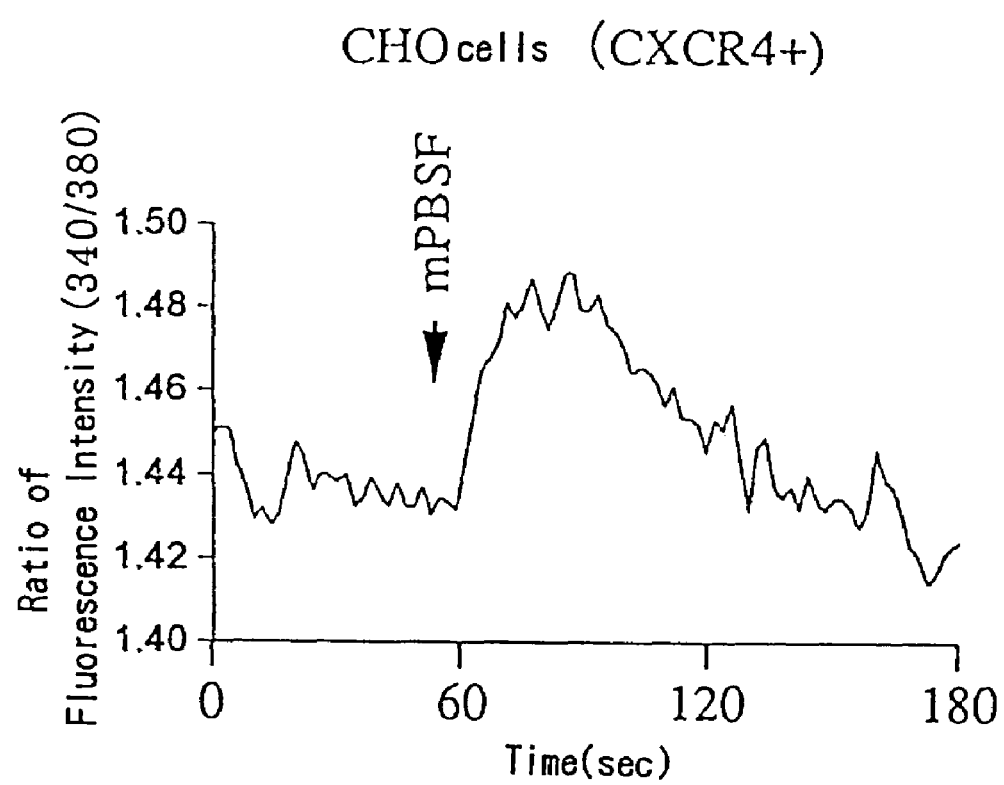
FIG. 6 is graphs each showing results of Example 6, wherein the abscissa indicates the passage of period of time, and the ordinate indicates the ratio of fluorescence intensities ([fluorescence intensity at 340 nm]/[fluorescence intensity at 380 nm]). The cells used are CHO cells in which the human chemokine receptor CXCR4/fusin/HUMSTSR is expressed.

The DNA of the present invention is not particularly limited as long as it is a DNA encoding a murine PBSF/SDF-1 receptor (murine CXCR4), which is a novel murine CXC chemokine receptor. Concretely, the following DNAs are exemplified:

1) a DNA encoding a polypeptide comprising an entire sequence of the amino acid sequence as shown by SEQ ID NO: 2 or a partial sequence thereof, or a polypeptide comprising the polypeptide described above, wherein any of the polypeptides has an activity of a receptor capable of binding to a murine PBSF/SDF-1;
2) a DNA encoding a polypeptide resulting from at least one of deletion, addition, insertion, or substitution of one or more amino acid residues in an entire sequence of the amino acid sequence as shown by SEQ ID NO: 2 or a partial sequence thereof, wherein any of the polypeptides has an activity of a receptor capable of binding to a murine PBSF/SDF-1;
3) a DNA comprising an entire sequence of the nucleotide sequence as shown by SEQ ID NO: 1 or a partial sequence thereof, or a DNA comprising the DNA, wherein any of the DNAs encodes a polypeptide having an activity of a receptor capable of binding to a murine PBSF/SDF-1;
4) a DNA resulting from at least one of deletion, addition, insertion, or substitution of one or more bases in a DNA comprising an entire sequence of the nucleotide sequence as shown by SEQ ID NO: 1 or a partial sequence thereof, or a DNA comprising the DNA, wherein any of the DNA encodes a polypeptide having an activity of a receptor capable of binding to a murine PBSF/SDF-1; and
5) a DNA being capable of hybridizing under stringent conditions with the DNA of any one of items 1) to 4) above, and encoding a polypeptide having an activity of a receptor capable of binding to a murine PBSF/SDF-1.

In addition, in item 2), the phrase "deletion, addition, insertion, or substitution of one or more amino acid residues" is not particularly limited, which, for instance, refers to deletion, addition, insertion, or substitution of one or several amino acid residues. Here, the term "several" refers, for instance, to a number of 10 or less. Further, in item 4), the extent of deletion, addition, insertion, or substitution of the bases of the DNA of the present invention is one or more bases, preferably one to several bases. Here, the term "several" refers, for instance, to a number of 10 or less. In addition, as long as the function or activity of the polypeptide to be expressed is of the same level, there may be included amino acid residues or bases which are chemically or biochemically modified, or non-naturally occurring or derivatized.

The DNA of the present invention can be isolated by amplifying a nucleotide sequence having homology with a known chemokine receptor by PCR, and screening a murine cDNA library using the amplified fragment as a probe.

An experimental method which can be employed in the present invention involves general procedures employed in molecular biology (DNA electrophoresis, a method of recovery of an electrophoretically separated DNA from a gel, ligation, host transformation, culture of recombinant host, plasmid DNA preparation, DNA cleavage with restriction enzymes, DNA radiolabelling and the like) which are well known to one of ordinary skill in the art, including, for instance, those described in *Molecular Cloning 2nd Ed.* [Maniatis et al., Cold Spring Harbor Laboratory, New York (1989)].

The primer used in PCR includes those obtained on the basis of an amino acid sequence conserved in a reported human chemokine receptor, and, for example, added with an appropriate restriction enzyme site on a 5'-side of a condensed forward primer to a DNA sequence encoding an amino acid sequence of a second transmembrane-spanning domain; or added with an appropriate restriction enzyme site on a 5'-side of a condensed reverse primer to a DNA sequence encoding an amino acid sequence of a seventh transmembrane-spanning domain. These primers can be synthesized with a DNA synthesizer.

Also, the murine mRNA used in a cDNA cloning can be purified from cells from, for instance, a murine pre-B-cell line DW34 (provided by Prof. Nishikawa of Kyoto Univ.), and the like with a commercially available mRNA purification kit.

In addition, the murine genomic DNA cloning can be performed by using, for instance, a DNA fragment derived from a cDNA of a murine CXCR4, and the like.

The nucleotide sequence of a cDNA or the nucleotide sequence of a genomic DNA thus obtained is subjected to its nucleic acid homology search, referring to, for example, GenBank/EMBL/DDBJ DNA sequence data base, and whereby whether or not the cDNA obtained encodes a chemokine receptor can be deduced. SEQ ID NO: 1 in Sequence Listing shows the nucleotide sequence of the cDNA obtained. Since the nucleotide sequence spanning from 120-position to 1196-position in SEQ ID NO: 1 is the longest open reading frame, the amino acid sequence (SEQ ID NO: 2) deduced on the basis of the nucleotide sequence of this open reading frame is subjected to its homology search, using a program such as DNASIS (HITACHI, LTD.) or BLAST [Altschul, F. et al., *J Mol. Biol.,* 215, 403-410], to a database such as Genbank, EMBL or DDBJ, whereby the polypeptide encoded by the DNA of the present invention can be further studied.

As a result, the polypeptide having the amino acid sequence as shown by SEQ ID NO: 2 has been deduced to be a trimer G protein-coupled receptor covering a seven transmembrane-spanning domain, characteristic to a chemokine receptor. In addition, as a result of comparison with the amino acid sequences of known CXC chemokine receptors, there has been revealed that a human CXCR4/fusin/HUMSTSR is most closely resembles it (90% identity).

In addition, since cells in which the DNA of the present invention is expressed have had receptor activity to a chemokine (murine PBSF/SDF-1) as well as an intracellular calcium level-increasing activity, the DNA of the present invention has been found to encode the novel murine chemokine receptor, and the protein encoded by this DNA is named a murine CXCR4.

The term "chemokine" refers to, among causative substances for which leukocytes show chemotactic activity to the local inflammation reaction as described above, a family of polypeptides having certain degrees of selectivity for migrating leukocytes and having four characteristic cysteine residues. These polypeptides are related with each other in their amino acid sequences and the biological activities. Four cysteine residues of a chemokine form disulfide bonds respectively between the first and third residues and between the second and fourth residues. The chemokine carrying another amino acid between the first and second cysteine residues is referred to as a "CXC chemokine," which is differentiated from the chemokine which has no additional amino acids referred to as "CC chemokine." Generally, there has been known that the CC chemokine has a chemotactic activity on a monocyte, but not on a neutrophile, and that the CXC chemokine has a chemotactic activity on a neutrophile, but not on a monocyte.

The term "chemokine receptor" refers to a family of cell membrane proteins bound specifically to the chemokines described above. The chemokine receptors are related with each other in their amino acid sequences and structures. All of the chemokine receptors have a seven transmembrane-spanning-domain characteristic to a rhodopsin family and a binding domain with a trimer G protein. The chemokine receptors are classified into two subgroups on the basis of the specificities to ligands. Among the chemokines described above, one bound specifically to the CXC chemokine is referred to as a "CXC chemokine receptor," which is differentiated from a "CC chemokine receptor" which is bound specifically to the CC chemokine. Generally, a chemokine receptor has an intracellular calcium level-increasing activity when bound to the respective ligand. Recently, there have been clarified that some chemokine receptors have not only an activity as a chemokine receptor but also an activity as an HIV-1 receptor by acting cooperatively with a molecule called CD4 which is present on a cell membrane.

In the present specification, the receptor activity to a murine PBSF/SDF-1 can be determined, for instance, in a manner as described below.

A PBSF/SDF-1 peptide which is a murine CXCR4 ligand is labeled with $^{125}I$ using, for example, BOLTON-HUNTER reagent, or is labeled with an enzyme such as an alkaline phosphatase. The labeled PBSF/SDF-1 peptide is added to a suspension of cells expressing a polypeptide having receptor activity, and incubated at a given temperature. After washing, the amount of the PBSF/SDF-1 peptide bound to the cells can be determined by quantifying the label, whereby assaying the receptor activity. Examples of the cells used herein are a murine pre-B-cell line DW34; human fetal kidney cell line 293 cells, or CHO cells derived from a Chinese hamster ovary cell line treated so as to express a murine CXCR4, and the like.

In addition, it is preferable that the polypeptide of the present invention has an activity of increasing the level of the intracellular calcium ions when bound to the ligand. The above activity can, for instance, be determined as described below.

The cells expressing the polypeptide, the subject for measurement of the above activity, are washed with a buffer, and the washed cells are suspended in an appropriate buffer [comprising, for instance, HBSS (20 mM Hepes, 125 mM NaCl, 5 mM KCl, 1 mM $MgCl_2$, 0.5 mM glucose, and 0.1% BSA at pH 7.4)]. A fluorescence reagent which is likely to be affected by the intracellular calcium ions is added to the suspension and incubated, so that the cells can be labeled. The labeled cells are washed with a buffer, and subsequently suspended in an appropriate buffer, so that the activity can be determined from the changes in the fluorescence intensities when a chemokine, which is a ligand, is added.

For instance, when fura-PE3AM (Texas Fluorescence Laboratories) is used as a fluorescence reagent, the determination is taken under conditions such that excitation wavelengths are 340 nm and 380 nm, a fluorescence wavelength is 510 nm, and a response is 0.5 seconds. Thereafter, the ratio of [fluorescence intensity at an excitation wavelength of 340 nm] to [fluorescence intensity at an excitation wavelength of 380 nm] is calculated. When the level of the intracellular calcium ions is increased in the cells to be measured by the addition of a chemokine, an increase in the ratio of the fluorescence intensities can be found. In addition, by adding different kinds of chemokines, the receptor specificities to the ligands can be also confirmed.

In addition, the presence of the mRNA in the murine CXCR4 can be confirmed by employing a usual mRNA specific detection method. For instance, the mRNA can be detected by Northern blotting analysis or in situ hybridization method by using an antisense RNA or cDNA as a probe. Alternatively, the mRNA can be also detected by converting an mRNA to a cDNA with a reverse transcriptase, and then performing PCR by an appropriate combination of primers.

Polypeptide of the Present Invention

The polypeptide of the present invention includes, for instance, the following:

1) a polypeptide encoded by the DNA of the present invention, wherein the polypeptide has an activity of a receptor capable of binding to a murine PBSF/SDF;
2) a polypeptide comprising an entire amino acid sequence as shown by SEQ ID NO: 2 or a partial sequence thereof, or a polypeptide comprising the polypeptide described above, wherein any of the polypeptides has an activity of a receptor capable of binding to a murine PBSF/SDF;
3) a polypeptide resulting from at least one of deletion, addition, insertion, or substitution of one or more amino acid residues in an entire amino acid sequence as shown by SEQ ID NO: 2 or a partial sequence thereof, wherein the polypeptide has an activity of a receptor capable of binding to a murine PBSF/SDF; and
4) the polypeptide according to any one of items 1) to 3) above, derived from a murine pre-B-cell line DW34.

In Embodiment 3), the extent of deletion, addition, insertion, or substitution of the amino acid residues of the polypeptide of the present invention is one or more, and the number of mutation is not particularly limited as long as the polypeptide has an activity of a receptor capable of binding to a murine PBSF/SDF-1. For instance, the number of mutations may be from one to several. Here, the term "several" refers to a number of, for instance, 10 or less. In addition, as long as the function or activity of the polypeptide is of the same level, there may be encompassed amino acid residues which are chemically or biochemically modified, or non-naturally occurring or derivatized.

In addition, it is preferable that the polypeptide of the present invention is those derived from a murine pre-B-cell line DW34.

The presence of the polypeptide of the present invention can be confirmed by employing a usual detection method for a specific protein, including, for instance, usual immuno-precipitation method, Western blotting method, or analysis by FACS each using an antibody specific to a murine CXCR4.

Expression Vector and Transformant of the Present Invention

The expression vector of the present invention can be obtained by, for example, incorporating the DNA of the present invention into a known vector such as pEFBOS, pCAGGStkNeo, or pMX.

In addition, the transformant of the present invention can be obtained by introducing the expression vector of the present invention into a desired host. The host is not particularly limited, and is preferably a mammalian cell line. Examples of the mammalian cell line are a murine pre-B-cell line, a human fetal kidney cell line, a cell line derived from a Chinese hamster ovary, and the like, and the cell line derived from a hamster ovary is preferable. A method for introducing an expression vector into a host may be any known method, including, for instance, such as a calcium phosphate method, a DEAE dextran method and an electroporation method.

In addition, the transformant described above is cultured under conditions capable of expressing the expression vector, whereby producing a polypeptide having an activity of a receptor capable of binding to the murine PBSF/SDF-1. The polypeptide produced in the manner described above can readily be purified by a usual column chromatography or an affinity chromatography using the antibody of the present invention.

Monoclonal Antibody of the Present Invention

Examples of the monoclonal antibody of the present invention are ones against the murine CXCR4 polypeptide and ones against a fusion protein of the above polypeptide with a human CXCR4/fusin/HUMSTSR.

The above monoclonal antibody can be prepared by a method described below.

As an immunogen, there are employed a synthetic polypeptide prepared by a usual peptide synthesizer based on a part of the amino acid sequence of the polypeptide of the present invention, or a murine CXCR4 produced by bacterial cells, yeasts, animal cells and insect cells which have been transformed with a vector expressing a murine CXCR4 in the form of cells themselves or a protein obtained by purifying with a usual protein chemistry technique. The above immunogen is used to immunize an animal such as a mouse, a rat, a hamster, a rabbit, or the like, and cells are collected from a spleen or a lymph node to be fused with myeloma cells, to prepare a hybridoma in accordance with a method described in Koehler and Milstein [*Nature*, 256, 495497 (1975)] or a modification thereof described in Ueda et al. [*Proc. Natl. Acad Sci. USA*, 79, 4386-4390 (1982)]. The hybridoma can produce a monoclonal antibody.

More concretely, for example, a monoclonal antibody to a murine CXCR4 can be obtained by the following steps.

(a) immunizing a mouse with a murine CXCR4 protein;
(b) enucleating an immunized murine spleen and separating spleen cells;
(c) fusing separated spleen cells with murine myeloma cells in the presence of a fusion enhancing agent (for example, polyethylene glycol) in accordance with a method described in Koehler et al. above;
(d) culturing hybridoma cells obtained in a selection medium in which non-fusion myeloma cells do not grow;
(e) selecting desired antibody-producing hybridoma cells by means of ELISA method, an immunoelectrotransfer method, and the like, and cloning the cells by a limiting dilution method; and
(f) collecting an anti-mouse murine CXCR4 monoclonal antibody.

In addition, the monoclonal antibody against a fusion protein of a murine CXCR4 with a human CXCR4/fusin/HUMSTSR is also encompassed in the present invention.

The monoclonal antibody mentioned above can be obtained by producing a fusion protein of a murine CXCR4 with a human CXCR4/fusin/HUMSTSR, and performing the above techniques with the resulting protein or a peptide thereof as an immunogen.

Pharmaceutical Composition and Cells of the Present Invention

The pharmaceutical composition of the present invention for the use as an AIDS onset inhibitor or an HIV-1 infection inhibitor comprises a murine PBSF/SDF-1.

The pharmaceutical composition of the present invention can be administered orally or parenterally. In other words, the pharmaceutical composition can be orally administered in a form which is usually used for administration, including, for instance, tablets, capsules, granules, powder, and the like, or alternatively the pharmaceutical composition can be injected intramuscularly or subcutaneously in the form of liquid, emulsion, suspension, liposome, and the like. In addition, the pharmaceutical composition can be administered to rectum as a suppository. These preparations can be produced by formulating the effective ingredients of the present invention with usual carriers, excipients, binding agents, stabilizers, buffers, dissolution auxiliaries, isotonic agents, and the like, which are pharmaceutically acceptable.

The dosage and the number of administration may differ depending on symptoms, case history, ages, body weights, forms of administration, and the like of the patients. For example, when orally administered to an adult, it can be administered at once or divided in several portions by appropriately adjusting the dosage to a range of usually from 5 to 500 mg, preferably from 10 to 100 mg, per one day.

In addition, the cells of the present invention are cells expressing the polypeptide of the present invention described above, or cells expressing both of the above polypeptide and a human CD4 protein.

The above cells can be obtained, for instance, by the following method. Specifically, a vector into which a polynucleotide encoding a murine CXCR4 is incorporated is obtained. As the vector, any of those known per se, such as pEFBOS, pCAGGS, and pMX can be used. Thereafter, the vector described above into which the polynucleotide is incorporated, is introduced into cells to be expressed, whereby obtaining the cells of the present invention. As the cells to be expressed, there can be included a cell line derived from a Chinese hamster ovary, CHO cells, a human colon cancer cell line, SW480 cells, a human osteoblastsarcoma cell line, HOS cells, a human glioblastoma cell line, U87MG cells, and the like. In addition, a method of introducing a vector includes, for instance, a calcium phosphate method and methods using Lipofectin (GibcoBRL) and Lipofectamine (GibcoBRL).

Since a murine CXCR4 is found to be an HIV-1 coreceptor, the cells of the present invention can be used to screen AIDS onset inhibitors, HIV-1 infection inhibitors, and PBSF/SDF-1 agonists and antagonists, to detect an AIDS onset or an HIV-1 infection, and the like.

Screening Method of the Present Invention

The screening method of the present invention includes a method of screening AIDS onset inhibitors, HIV-1 infection inhibitors, and murine or human PBSF/SDF-1 agonists and antagonists. Concretely, the following methods are illustrated.

1) A method of screening an AIDS onset inhibitor or an HIV-1 infection inhibitor, characterized in that the method comprises the steps of:
   (a) mixing the cells of the present invention described above; a human T-cell-line-tropic HIV-1; and a substance to be screened, and incubating the resulting mixture; and
   (b) analyzing localization of an HIV-1 in the cells.
2) A method of screening an AIDS onset inhibitor or an HIV-1 infection inhibitor, characterized in that the method comprises the steps of:
   (a) mixing the cells of the present invention described above; cells expressing an HIV-1 envelope protein; and a substance to be screened, and incubating the resulting mixture; and
   (b) determining a level of the fusion of the above cells with the cells expressing an HIV-1 envelope protein.
3) A method of screening an AIDS onset inhibitor or an HIV-1 infection inhibitor, or a PBSF/SDF-1 agonist or antagonist, characterized in that the method comprises the steps of:
   (a) mixing the cells of the present invention described above; a murine or human PBSF/SDF-1; and a substance to be screened, and incubating the resulting mixture; and
   (b) determining an intracellular calcium ion level and/or determining a binding activity of an expressed polypeptide with the murine or human PBSF/SDF-1.

In addition, as a human T-cell-line-tropic HIV-1, there can be included an HIV-1 IIIB strain (provided by Prof. Harada of Kumamoto Univ.) and an HIV-1 NL432 strain (provided by Prof. Adachi of Tokushima Univ.).

Embodiment 1

It is more preferable that the step for analyzing the localization of an HIV-1 is carried out with a monoclonal antibody against a human T-cell-line-tropic HIV-1.

The method of analysis using the above monoclonal antibody is not particularly limited, and includes any known usual method.

In addition, as the method for analyzing the localization of an HIV-1, the following enzyme method may also be employed.

Specifically, as "the cells of the present invention" used in this method, those preferably used are cells expressing a human CD4 protein and a coreceptor (for instance, SW480, U87MG, HOS, and the like) in which a gene for an enzyme (such as β-galactosidase, luciferase, or CAT) is introduced downstream of LTR, which is an expression promoter of an HIV-1 gene. When the cells are infected with an HIV-1, a tat protein, which is one kind of viral proteins, is expressed which in turn activates LTR. Accordingly, the infection level can be quantified by determining the enzymatic activity in the cell lysate.

Embodiment 2

As the cells expressing an HIV-1 envelope protein, there can be included, for instance, ones in which an HIV-1 envelope protein gene is introduced into an HeLaS3. Further, ones in which, for instance, a β-galactosidase subunit (either one of α or ω) gene is additionally introduced are preferably used. In addition, as "the cells of the present invention," there can be preferably used, for example, ones in which a human CD4 protein and a coreceptor are introduced into an NIH3T3; and ones in which a β-galactosidase subunit (either one of α or ω), and different from that introduced into the cells expressing an HIV-1 envelope protein) gene is additionally introduced. When the cells expressing an HIV-1 envelope protein and the cells of the present invention are subjected to cell fusion, β-galactosidase α-subunit and ω-subunit are associated to form an active β-galactosidase. Accordingly, the cell fusion level can be measured by mixing the cells of both parties, culturing them, and then determining the galactosidase activity in the cell lysate.

Embodiment 3

When an activity for increasing an intracellular calcium ion level is observed as a result of the incubation in Step (a), it is possible that the substance to be screened is an agonist. When the binding between the substance to be screened and a receptor is observed even though no increase in the activity for intracellular calcium ion level is observed, it is possible that the substance to be screened is an antagonist. In addition, when there are influences in the activity for increasing an intracellular calcium ion level of a murine PBSF/SDF-1 and/or on a binding activity with a receptor, i.e., the activities are inhibited, it is possible that the substance to be screened is an antagonist. In addition, the above antagonist is exemplified by a hematopoetic stem cell liberator.

Detection Kit and Detection Method

The kit for detecting an AIDS onset or an HIV-1 infection of the present invention is characterized in that the kit comprises the cells of the present invention.

By using the above kit, an AIDS onset or an HIV-1 infection can readily be detected. The kit of the present invention is intended to perform the detection using the method for detection of the present invention described below.

The method for detecting an AIDS onset or an HIV-1 infection of the present invention is characterized in that the method comprises;

(a) mixing the cells of the present invention described above with sera, blood cells or blood of a patient suspected to be infected with an HIV-1, and incubating the resulting mixture, and (b) analyzing localization of an HIV-1 in the cells or determining a level of the fusion of the cells with HIV-1-infected cells.

As the method for analyzing localization of an HIV-1 used herein, there are included ones employed in an AIDS onset inhibitor or an HIV-1 infection inhibitor of the present invention. In addition, as the method of determining a level of the fusion of the cells with HIV-1-infected cells, there are included ones employed in an AIDS onset inhibitor or an HIV-1 infection inhibitor of the present invention. Incidentally, the term "HIV-1-infected cells" in Step (b) refers to HIV-1-infected blood cells of a patient suspected to be infected with an HIV-1.

Utility of the Present Invention

Both of a murine CXCR4 and a human CXCR4/fusin/HUMSTSR of the present invention react with a murine PBSF/SDF-1. Since there is a difference of only one amino acid out of 71 amino acids in the murine and human PBSF/SDF-1s, a murine CXCR4 is expected to be bound also with a human PBSF/SDF-1. Since a human PBSF/SDF-1 inhibits an infection with a T-cell-line-tropic HIV-1 mediated by a CXCR4/fusin/HUMSTSR, an antibody against the murine CXCR4 protein of the present invention and an antibody against a chimera protein having a binding site with a T-cell-line-tropic HIV-1 resulting from mutual substitution of the extracellular domains of a murine CXCR4 and a human CXCR4/fusin/HUMSTSR can be used as an HIV-1 infection inhibitor, i.e., a therapeutic agent against AIDS.

By means of the method of screening agonists and antagonists of a chimera protein resulting from mutual substitution of the extracellular domains of a murine CXCR4 protein, and murine CXCR4 and human CXCR4/fusin/HUMSTSR provided by the present invention, such agonists and antagonists can be obtained, each of which can be used as an HIV-1 infection inhibitor, i.e., a therapeutic agent against AIDS.

The present invention will be described in further detail by means of the following working examples, but the present invention is by no means limited to these examples.

EXAMPLES

Example 1

Cloning of cDNA of Murine CXCR4

(1) Synthesis of Primer

Based on a known amino acid sequence of a chemokine receptor, a condensed forward primer C2F2-2 (SEQ ID NO: 9) to a DNA sequence encoding an amino acid sequence of a second transmembrane-spanning domain, and a condensed reverse primer C4R1 (SEQ ID NO: 10) to a DNA sequence encoding an amino acid sequence of a seventh transmembrane-spanning domain were synthesized using a DNA synthesizer ("Cyclone Plus," Nippon Millipore).

(2) Purification of mRNA from Murine Pre-B-Cell Line DW34

A murine pre-B-cell line DW34 was suspended in RPMI 1640 medium. After culturing for one week, the culture was washed with Dulbecco PBS(−) [Nissui], and mRNA was purified by using mRNA Purification Kit (Pharmacia).

(3) Cloning of cDNA Fragment of Murine CXCR4

A single-stranded cDNA was synthesized from 200 ng of mRNA purified from a murine pre-B-cell line DW34 with Ready-To-Go T-Primed First-Strand Kit (Pharmacia). PCR reaction (30 cycles under conditions of 94° C. for 0.5 minutes, 55° C. for 0.5 minutes, and 72°C. for 1 minute) was carried out using the resulting single-stranded cDNA as a template, C2F2-2 and C4R1 as primers, and Taq as a thermostable DNA polymerase. The resulting reaction mixture was separated by low-melting point agarose gel electrophoresis, and a DNA band of a desired size (about 690 bp) was excised, and a DNA fragment was purified by using Wizard PCR Preps DNA Purification System (Promega). The resulting DNA fragment was inserted into pT7Blue vector by using a DNA Ligation Kit (Takara). The nucleotide sequence of the inserted DNA was determined by PRISM Ready Reaction Sequence Kit (Applied Biosystems) and DNA Sequencer (Applied Biosystems). The resulting cDNA sequence of a murine CXCR4 is shown by SEQ ID NO: 3. Based on the cDNA sequence of a murine CXCR4 obtained in the manner described above, primers as shown by SEQ ID NO: 11 and as shown by SEQ ID NO: 12 were synthesized, and a cDNA clone containing 5'-terminal was obtained using the cDNA of DW34 cells obtained as described above as a template, with Marathon cDNA Amplification Kit (Clontech). The resulting cDNA sequence of a murine CXCR4 is shown by SEQ ID NO: 5.

Example 2

Expression of Murine CXCR4 in Each Tissue (1) Preparation of Probe

In order to study the expression of a murine CXCR4 in each murine tissue, firstly, a probe was prepared as follows. Based on the nucleotide sequence of a murine CXCR4 gene, a DNA sequence (SEQ ID NO: 19) in the same direction corresponding to the second transmembrane-spanning-domain portion, and a DNA sequence (SEQ ID NO: 20) in the opposite direction corresponding to the seventh transmembrane-spanning-domain portion were synthesized as primers to be used in the subsequent PCR. PCR reaction was carried out for 30 cycles under conditions of 94° C. for 1 minute, 55° C. for 1 minute, and 72° C. for 2 minutes, using the cDNA of the nucleotide sequence obtained in Item (3) of Example 1 above as a template, and a Taq Polymerase. The resulting reaction mixture of the PCR was separated by agarose gel electrophoresis, and a DNA band of a desired size (about 690 bp) was excised, and a DNA fragment was purified by using Wizard PCR Preps DNA Purification System. Fifty nanograms of the resulting DNA fragment was $^{32}$P-labeled by using Prime-It II Random Primer Labelling Kit (Stratagene) to be used as a probe.

(2) Northern Blotting Analysis of Murine Tissue and Murine Fetus mRNAs Of various murine tissues and mRNAs of murine fetuses of 7 days, 11 days, 15 days and 17 days after embryogenesis were separated by electrophoresis, and the transferred membrane and the probe obtained in Item (1) above were subjected to hybridization. The membrane was washed by immersing in 2×SSC containing 0.05% SDS at room temperature for 15 minutes twice, and further immersing in 0.1×SSC containing 0.1% SDS at 50° C. for 20minutes twice. The radioactive rays of this membrane were detected by autoradiography. The results are shown in FIG. 2 A (murine tissue) and B (murine fetus). It is clear from the intensities of the bands that strong signals were obtained at thymus, lymph node, and spleen, and week signals were obtained at brain, small intestine, stomach, and kidney. In addition, strong signals were obtained in the entire murine fetus.

Example 3

Cloning of Genomic DNA of Murine CXCR4

(A) Preparation of Probe

Based on the nucleotide sequence of a murine CXCR4 cDNA obtained in Item (3) of Example 1 above, appropriate forward and reverse primers were synthesized to be used in the subsequent PCR. A double-stranded DNA was obtained from the cDNA in Item (3) of Example 1, and PCR reaction was carried out using this double-stranded DNA as a template and a Taq polymerase. The reaction product was separated by agarose gel electrophoresis, and a DNA band of a desired size (about 690 bp) was excised, and a DNA fragment was purified. Fifty nanograms of the resulting DNA fragment was $^{32}$P-labeled using Prime-It II Random Primer Labelling Kit (Stratagene) as a probe.

(B) Cloning of Murine Genomic Library

First, with a 129/SvJ murine liver genomic library incorporated into a phage vector λFIXII was infected *Escherichia coli*, and as a primary screening, and spread over a plate to form a plaque, and the plaque was transferred to nylon membrane (Du Pont). This membrane was pre-hybridized by immersing the membrane in a pre-hybridization reagent [5×SSPE (0.9M NaCl, 0.05M sodium phosphate at pH 7.7, 0.005M Na$_2$EDTA), 50% formamide, 5×Denhardt's reagent, 50 μg/ml salmon sperm DNA, 0.1% SDS]. Thereafter, the pre-hybridized membrane was hybridized together with the probe obtained in Item (A) above at 42° C. for 15 hours by immersing the membrane in a hybridization reagent [5×SSPE, 50% formamide, 1×Denhardt's reagent, 10%-dextran disodium sulfate, 50 μg/ml salmon sperm DNA, 0.1% SDS]. After washing the membrane, the radioactivity was detected, and positive plaques giving signals were selected. The selected plaques were successively diluted to carry out secondary and tertiary screening, and whereby two single clones were selected.

The cloned phage DNA was cleaved with various restriction enzymes, and separated by agarose gel electrophoresis. Those bands having the same patterns were considered to be the same clone, and the cloned phage DNA was cleaved such that a positive band of the size as small as possible could be obtained by repeating the same hybridization. The selected positive DNA fragment was inserted into a pBluescripts KSII vector, and the nucleotide sequence was determined by dideoxy method. The resulting DNA sequence of the murine CXCR4 gene is shown by SEQ ID NO: 7. A nucleotide sequence containing the longest open reading frame was found from the nucleotide sequence as shown by SEQ ID NO: 5 and the nucleotide sequence as shown by SEQ ID NO: 7, and its nucleotide sequence is shown by SEQ ID NO: 1. Also, this nucleotide sequence as shown by SEQ ID NO: 1 was subjected to nucleic acid homology search with the GenBank/EMBL/DDBJ DNA sequence data base. As a result of the search, it was clarified that the resulting clone is a DNA encoding a novel murine chemokine receptor, and the clone was named murine CXCR4.

Example 4

Homology Analysis of Amino Acid Sequence of Murine CXCR4

The amino acid sequence (SEQ ID NO: 2) which was deduced based on the nucleotide sequence of a murine CXCR4 was estimated to be a trimer G protein-coupled receptor containing a seven transmembrane-spanning domain, characteristic to a chemokine receptor. The amino acid sequence thereof was compared with a known sequence of a CXC chemokine receptor (GenBank, EMBL, DDBJ were used as data base, and analyzed with BLAST). As a result, the analyzed sequence most closely resembled human CXCR4/fusin/HUMSTSR (90% identity), and homologies with monkey CXCR4 and bovine CXCR4 were 89% and 86%, respectively, and homologies with rat IL-8RB, rabbit IL-8RA, and rabbit IL-8RB were 49%, 47%, and 45%, respectively.

Example 5

Expression of Murine CXCR4 and Human CXCR4/fusin/HUMSTSR (1) Preparation for Expression Vectors of Murine CXCR4, Human CCCRR2B and
Human CXCR4/fusin/HUMSTSR In order to clone previously reported human chemokine receptors a CC CKR2B gene and a CXCR4/fusin/HUMSTSR gene, PCR reaction was carried out in the following manner using a cDNA of a human monocyte cell line THP-1. Five-hundred nanograms of a cDNA of the THP-1 cells was used as a template, the primers as shown by SEQ ID NO: 15 and SEQ ID NO: 16 were used for amplification of human CXCR4/fusin/HUMSTSR, and the primers as shown by SEQ ID NO: 13 and SEQ ID NO: 14 were used for amplification of CC CKR2B, each primer of which was used in an amount of 500 ng. As the enzyme for the reaction, Taq Polymerase (Takara Shuzo) was used. The reaction was carried out for 1 cycle at 94° C. for 3 minutes; thereafter, 35 cycles at 94° C. for 1 minute, 55° C. for 2 minutes, and 72° C. for 3 minutes; and further at 72° C. for 3 minutes. The gene fragments of human CXCR4/fusin/HUMSTSR and CC CKR2B obtained by the reaction were each incorporated into TA cloning sites of pCRII (Invitrogen). The plasmids obtained in the manner described above were named pCRIICXCR4 and pCRIICC CKR2B, respectively. Subsequently, the resulting pCRIICXCR4 and pCRIICC CKR2B plasmids were respectively digested with NotI and XboI (both from Takara Shuzo), and the digested fragment was incorporated into a NotI/XboI site of pCAGGStkNeo. The plasmids obtained in the manner described above were named pCANCXCR4 and pCANCC CKR2B, respectively.

In order to clone the murine CXCR4 gene, PCR technique was carried out using a single-stranded cDNA of the murine pre-B-cell line DW34 as shown by SEQ ID NO: 5 obtained in Item (3) of Example 1 above as a template. One hundred nanograms of the cDNA was used as a template, and the primers as shown by SEQ ID NO: 17 and as shown by SEQ ID NO: 18 were used. As the enzyme used for reaction, ExTaq (Takara Shuzo) was used. The reaction was carried out for 1 cycle at 94° C. for 3 minutes; thereafter, 20 cycles at 94° C. for 1 minute, 55° C. for 1 minute, and 72° C. for 2 minutes; and further at 72° C. for 5 minutes. The resulting murine CXCR4 gene fragment was digested with NotI and XhoI (Takara Shuzo), and the digested fragment was incorporated into a NotI/XboI site of pCAGGStkNeo. The plasmid obtained in the manner described above was named pCANmPBSFR.

(2) Expression of Murine CXCR4, Human CXCR4/fusin/HUMSTSR and Human CC CKR2B in CHO Cells CHO cells were cultured in a cell culture petri dish (Iwaki Glass Co., Ltd.) having a diameter of 10 cm at 37° C. for 2 day in the presence of 10% $CO_2$ gas. Each 30 µg of DNAs of expression vectors of the three chemokine receptors obtained in Item (1) above (pCANmPBSFR, pCANCXCR4 and pCANCC CKR2B) was dissolved in 25 µl of distilled water, and to the resulting mixed solution was added 500 µl of 250 mM calcium chloride (nacalaitesque). To the liquid mixture of the DNA and calcium chloride was added 500 µl of 2×BBS solution [50 mM BES (SIGMA), 280 mM sodium chloride (nacalaitesque) and 1.5 mM disodium hydrogenphosphate (nacalaitesque)], and then allowed to stand at room temperature for 25 minutes. The DNA solution prepared in the manner described above was added dropwise to the petri dish in which the CHO cells were cultured, and the cells were cultured at 35° C. for 20 hours in the presence of 3% $CO_2$ gas to introduce the DNA into the cells. The cells into which the DNA was introduced were washed twice with 3 ml of PBS(+), and thereto was added 10 ml of α-MEM (GIBCO) containing 10% FCS solution, and the cells were cultured at 37° C. for one day in the presence of 5% $CO_2$ gas.

Subsequently, the cells were suspended in a medium prepared by adding 2 mg/ml GENETICIN (Wako Pure Chemical Industries, Ltd.) to an a-MEM (GIBCO) medium containing 10% FCS, and divided into cell culture petri dishes (Iwaki Glass Co., Ltd.) each having a diameter of 10 cm at a cell density of $5 \times 10^3$ cells/petri dish. The culture was continued at 37° C. in the presence of 10% $CO_2$ gas, and GENETICIN-resistant cells were used for determination of an intracellular calcium level as CHO cell lines expressing a murine CXCR4, a human CXCR4/fusin/HUMSTSR, and CC CKR2B. As illustrated in Example 6 given below, since the CC CKR2B was found to have an activity of increasing the intracellular calcium level owing to the addition of a specific ligand MCP-1, the expression of the receptor was confirmed. In addition, the murine CXCR4 and the human CXCR4/fusin/HUMSTSR were also considered to be similarly expressed, because transformation and culture were carried out in the same manner using the same cell line as the CC CKR2B.

Example 6

Biological Activity of Murine CXCR4

Each of the CHO cells expressing the murine CXCR4 and the human chemokine receptors (CXCR4/fusin/HUMSTSR and CC CKR2B) obtained in Item (2) of Example 5 above was washed with Dulbecco PBS(−), and then suspended in an HBSS buffer (containing 125 mM NaCl, 5 mM KCl, 1 mM $MgCl_2$, 0.5 mM glucose and 0.1% BSA in 20 mM Hepes at pH 7.4) at a cell density of $5 \times 10^6$ cells/ml. To the resulting suspension was further added fura-PE3AM (Texas Fluorescence Laboratory) so as to have a concentration of 2.5 µM, and the cells were then incubated at 37° C. for 30 minutes. After washing with the HBSS buffer, each of the cells expressing CC chemokine receptor was suspended in the same buffer at a cell density of $5 \times 10^6$ cells/ml. The changes in the fluorescence when each chemokine (murine PBSF/SDF-1 or human MCP-1) was added to 500 µl of each of the resulting suspensions of the cells expressing CC chemokine receptor so as to have a concentration of 100 nM were determined with a spectrofluorophotometer (LS50B, PERKIN-ELMER) at the excitation wavelengths of 340 nm and 380 nm, the fluorescence wavelength of 510 nm and the response of 0.5 seconds. The results are shown in FIG. 3 to 6 which are represented in terms of the ratio of the fluorescence intensity at 340 nm and that at 380 nm over a passage of a time period.

Figure 7:
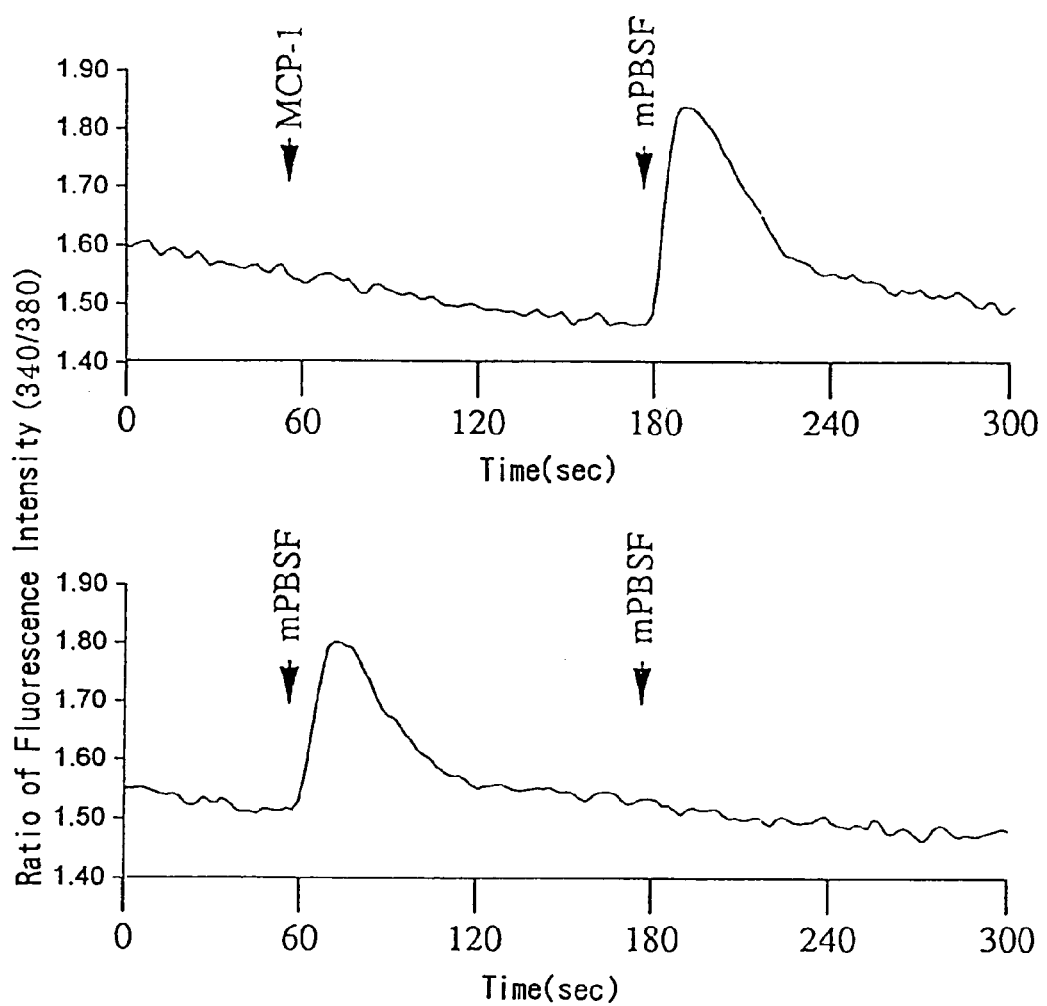
FIG. 7 is graphs each showing results of Example 6, wherein the abscissa indicates the passage of period of time, and the ordinate indicates the ratio of fluorescence intensities ([fluorescence intensity at 340 nm]/[fluorescence intensity at 380 nm]). The cells used are CHO cells in which a murine CXCR4 is expressed.

In the murine PBSF/SDF-1 stimulation, there was found to be an increase in the ratios of fluorescence intensity in the cells expressing a murine CXCR4 and a human CXCR4/fusin/HUMSTSR, while there was found to be no increase in the ratios of fluorescence intensities in the cells expressing CC CKR2B, which is a CC chemokine receptor. Incidentally, in the stimulation with a MCP-1 peptide, which is a positive control to a receptor, there was found to be an increase in the ratio of fluorescence intensities in the cells expressing CC CKR2B. Therefore, the murine PBSF/SDF-1 was found to have an activity of increasing the intracellular calcium ion level specifically to the CHO cells expressing the murine CXCR4 and the human CXCR4/fusin/HUMSTSR according to the present invention. Also, as shown in FIG. 7, in the cells expressing a murine CXCR4, the desensitization was found wherein there were no changes in the ratio of the fluorescence intensities by continuous addition of a murine PBSF/SDF-1. The desensitization was not found when a human MCP-1, a negative control, was added. From these results, it was clarified that the receptor of the present invention is the receptor of a murine PBSF/SDF-1 receptor.

Example 7

Materials and Methods

Cell lines: Murine NIH3T3 cells, SW480 cells derived from human small intestine epithelium, and U87MG derived from human gliacyte were cultured in DMEM containing 10% FCS. Human HeLaS3 cells were cultured in RPMI1640 containing 10% FCS. HOS cells derived from human osteoblasts were cultured in Eagle MEM containing 1% non-essential amino acids (Gibco) and 10% FCS.

Viruses: An HIV-1 NL432 strain was provided by Prof. Adachi (Tokushima Univ.). A IIIB strain was provided by Prof. Harada (Kumamoto Univ.). An SF162 strain was provided by Prof. J. A. Levy (San Francisco Univ., California). HIV-1 chimera virus clones, NL432env-162 and NL432V3-162 were provided by Isaka (Shionogi & Co., Ltd.). Recombinant vaccinia viruses, Vac. Env (NL432 env), Vac. Env 162 (SF162 env) and Vac T4 (CD4) were provided by Prof. Shioda (Tokyo Univ.). LO-T7 (T7 polymerase) was provided by M. Kohara (TORITSU RINSHOKEN).

Transfection to cells: NIH3T3 cells were cultured overnight in a 24-well plate at a cell density of $5 \times 10^4$ cells per well, and transfected with a chemokine receptor gene which was incorporated into pBluescript using Lipofectamine (Gibco). 4 Hours after initiation of the transfection, the cells were washed with PBS, and thereto a culture medium was added, and then cultured at 37° C. overnight to be subjected to a fusion assay. The SW480 cells and the HOS cells were cultured overnight in a 6 cm-plate at a cell density of $5 \times 10^5$ cells. The SW480 cells were transfected with a plasmid mixture of 5 μg of the receptor gene which was incorporated into pEF-BOS, 7.5 μg of T4-Neo, a vector expressing CD4, and 2.5 μg of LTR (EcoRV)-β-Gal-Neo by means of a modified calcium phosphate method. The HOS cells constitutively expressing a human CD4 and an LTR-Gal were transfected with 15 μg of a receptor gene which was incorporated into pEF-BOS by the same method. Each of the cells was cultured at 35° C. overnight in the presence of 3% $CO_2$, washed with PBS(−), and collected with PBS containing 0.5 mM EDTA. Thereafter, the culture was plated in over a 12-well plate, and cultured at 37° C. overnight to be subjected to an infection assay.

Cell fusion assay: In order to quantify the cell fusion, we employed a modified cell fusion assay utilizing α-complementation of β-galactosidase (β-gal) (Shida et al., manuscript in preparation).

A β-gal a-subunit and an env protein were introduced into HeLaS3 cells (24-well plate, $1 \times 10^5$ cells/well), which are effector cells, by using a recombinant vaccinia virus.

A human CD4, a β-gal ω-subunit, and a T7 RNA polymerase were introduced into NIH3T3 cells (24-well plate, $5 \times 10^4$ cells/well), which are target cells, by using a recombinant vaccinia virus, and a chemokine receptor was transfected to the target cells using Lipofectamine. 16 Hours after transfection, the effector cells and the target cells were washed with PBS containing 0.5 mM $CaCl_2$, and treated with 2D5, an anti-vaccinia virus antibody, in order to inhibit the non-specific cell fusion caused by the vaccinia virus. The effector cells were suspended in a Hanks buffer (pH 7.6) containing 3 mM $CaCl_2$, and overlayered on the target cells in the 24-well plate. Thereafter, the resulting overlayered mixture was centrifuged at 1,300 rpm for 5 minutes to initiate the cell fusion.

After centrifugation, the cells were cultured at 37° C. for 12 hours in the presence of 5% $CO_2$. When the cell fusion takes place, α-subunit and ω-subunit of the β-gal contained in the cytoplasmas of the fusion cells are associated with each other to form an active β-gal enzyme by a-complementation. Therefore, after the culture medium was removed, a solution containing 8 mM chlorophenolred-b-D-galactopyranoside (Boehringer Mannheim), which is a β-gal substrate, 45 mM 2-mercaptoethanol, 1 mM $MgCl^2$, 100 mM Hepes at pH 8.0, 0.5% NP40 and 0.1 mg/ml DNAse I was added in an amount of 200 μl per one well, and reacted at 37° C. for 30 minutes. Thereafter, 2% SDS was added in an amount of 200 μl per one well to terminate the reaction. In order to quantify the β-gal activity in the reaction mixture, the absorbance was measured at a wavelength of 590 nm.

Infection assay: The human SW480 or HOS cells each expressing a human CD4 and a receptor were cultured in a 12-well plate. To each well was added a culture containing an HIV-1 virus (reverse transcriptase (RT) activity: SF162: $2 \times 10^6$ RT/mL; NL432envl62, NL432V3-162 and IIIB: $5 \times 10^6$ RT/mL; NL432: $3 \times 10^6$ RT/mL), and cultured at 37° C. for 2 hours in the presence of 5% $CO_2$, and then the culture medium was added in an amount of 2.5 mL per one well. 4 Days after infection, a Reporter lysis buffer (Promega) was added in an amount of 400 μl per one well, frozen at −80° C., and then thawed. The thawed sample was transferred to an Eppendorf tube, and centrifuged at 12,000 rpm at 4° C. for 5 minutes. Thereafter, the β-gal activity contained in the supernatant was measured with a luminescence β-gal detection kit (Clontech).

Results

Figure 8:
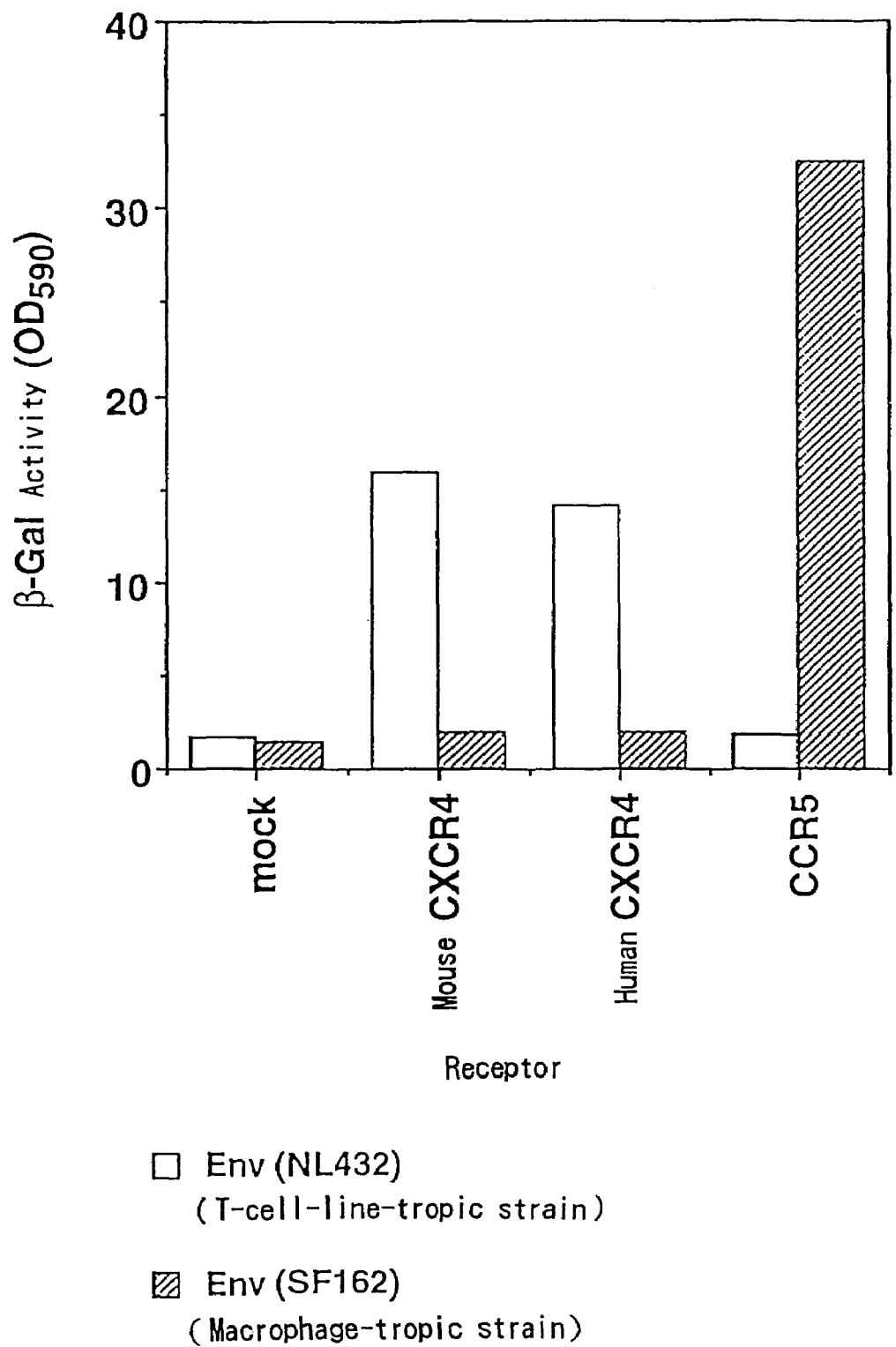
FIG. 8 is a graph showing that a murine CXCR4 supports a membrane fusion via env protein derived from a human T-cell-line-tropic HIV-1 strain. NIH3T3, which is target cells, is subjected to infection with a recombinant vaccinia virus in which human CD4, T7 polymerase, and an ω-subunit of β-gal are expressed. After infection, these cells are transfected with a murine CXCR4, a human CXCR4, or a human CCR5. HeLaS3, which is effector cells, is subjected to infection with a recombinant vaccinia virus in which env protein derived from NL 432 or SF 162 and an α-subunit of β-gal are expressed. After the resulting infected cells are subjected to cell fusion, the resulting fusion product is subjected to β-gal assay.

First, in order to study whether or not a murine CXCR4 supports an env-mediated cell fusion of an HIV-1, we conducted an experiment using an assay system in which β-Gal is activated by the fusion of the effector cells (HeLaS3 cells) expressing an env protein with the target cells (NIH3T3 cells) expressing a human CD4 and a receptor. In this assay, the HeLaS3 cells, effector cells, were subjected to infection with a recombinant vaccinia virus to express an α-subunit of the β-Gal and an HIV-1 env protein, and the NIH3T3 cells, target cells, were subjected to infection with a recombinant vaccinia virus to express an ω-subunit of the β-Gal, a T7 polymerase and a human CD4. After infection with a virus, the NIH3T3 cells were further transfected with a plasmid carrying a human CXCR4, a human CCR5, or a murine CXCR4. After an overnight culture, the effector cells and the target cells were mixed and cultured. When the cell fusion takes place, the α-subunit and the ω-subunit of the β-Gal contained in the cytoplasmas of the fusion cells are associated with each other, whereby activating the β-Gal. As shown in FIG. 8, the HeLaS3 cells expressing an env protein derived from NL432, a T-cell-line-tropic HIV-1, are fused with the NIH3T3 cells expressing a human CXCR4 and a human CD4, but not with the NIH3T3 cells expressing a human CCR5 and a human CD4.

Surprisingly, the HeLaS3 cells expressing an env protein derived from NL432 are also fused with the cells expressing a murine CXCR4 and a human CD4 similarly. The HeLaS3 cells expressing an env protein derived from SF162, a monocyte-tropic HIV-1, are fused with the NIH3T3 cells expressing a human CCR5 and a human CD4, but not with the NIH3T3 cells expressing a human CXCR4 or a murine CXCR4 and a human CD4.

Figure 9:
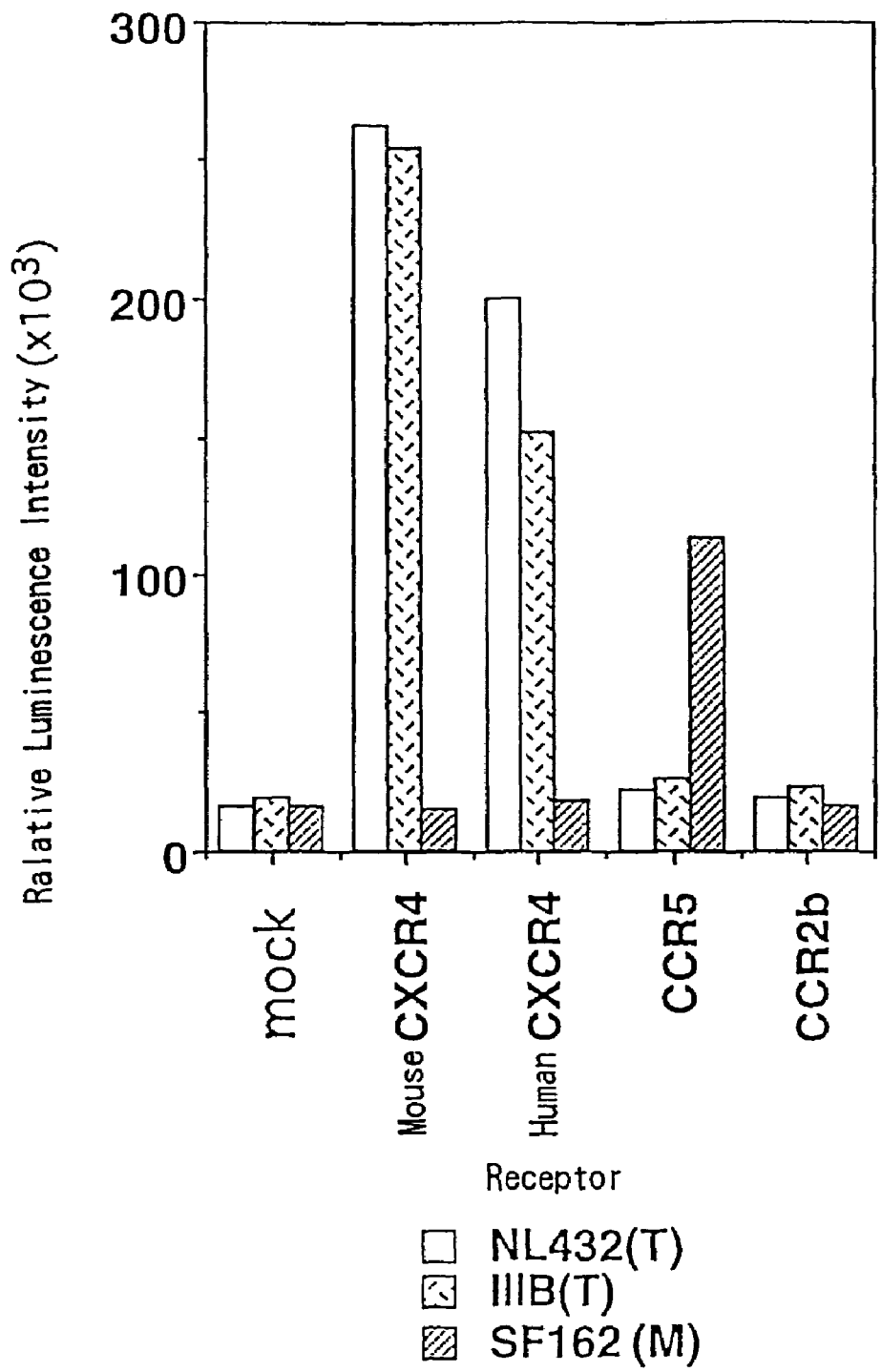
FIG. 9 is a graph showing that a murine CXCR4 supports an infection with a human T-cell-line-tropic HIV-1 virus. SW480 cells (A) are transfected with a human CD4, and each of chemokine receptors (murine CXCR4, human CXCR4, human CCR5, and human CCR2b). The resulting transfected cells are subjected to infection with each of NL432 strain, IIIB strain and SF162 strain of HIV-1. A cell lysate of each of the resulting infected cells is then subjected to β-gal assay.

Second, we have studied whether cells which expressed a murine CXCR4 were infected with a virus. Since murine cells which expressed human CXCR4 and CD4, including NIH3T3 cells, had a low HIV-1 replication efficiency, three human cell lines, namely, the SW480 cells derived from human small intestine epithelium, the HOS cells derived from osteoblasts, and the U87MG cells derived from human gliacytes were used as the target cells for viral infection. These cells were transfected with a reporter gene (lacZ) having an LTR of an HIV-1 as a promoter. When the cells are infected with a virus, Tat protein, which is a transcription-activating factor derived from an HIV-1, is expressed to act on an LTR, whereby inducing the expression of lacZ. These cells were further transfected with a human CD4 and a chemokine receptor, and then subjected to infection with a T-cell-line-tropic virus strain (NL432, IIIB) or a monocyte-tropic virus strain (SF162). As shown in FIG. 9, with NL432 and IIIb were infected similarly both of SW480 expressing a murine CXCR4 and a human CD4, and SW480 expressing a human CXCR4 and a human CD4. These findings were consistent with the results of the fusion assay described above. On the contrary, when the human CCR2b or CCR5 was expressed instead of CXCR4, the cells were not infected with these viruses.

Figure 10:
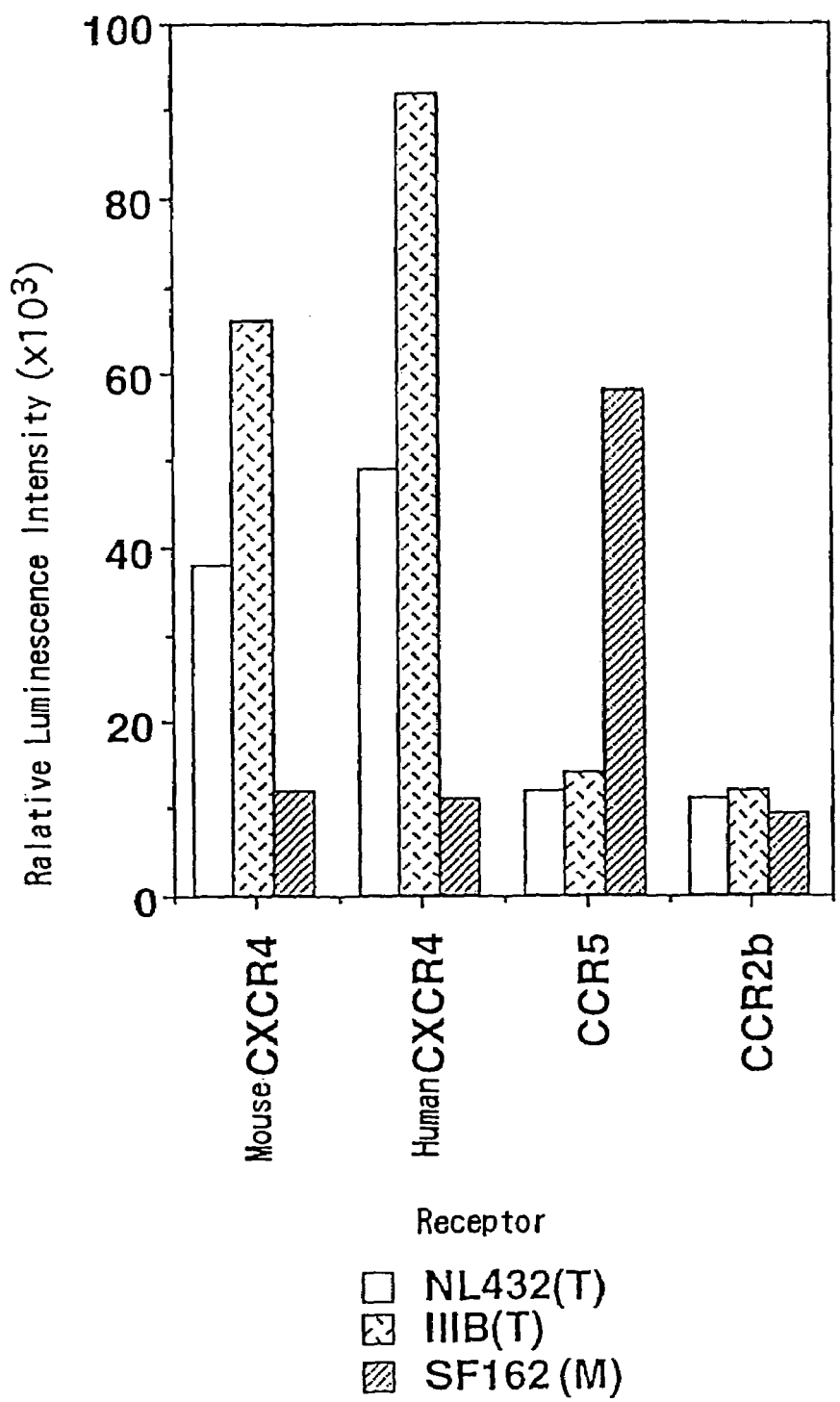
FIG. 10 is a graph showing that a murine CXCR4 supports an infection with a human T-cell-line-tropic HIV-1 virus. HOS cells (B) are transfected with a human CD4, and each of chemokine receptors (murine CXCR4, human CXCR4, human CCR5, and human CCR2b). The resulting transfected cells are subjected to infection with each of NL432 strain, IIIB strain and SF162 strain of HIV-1. A cell lysate of each of the resulting infected cells is then subjected to β-gal assay.
Figure 11:
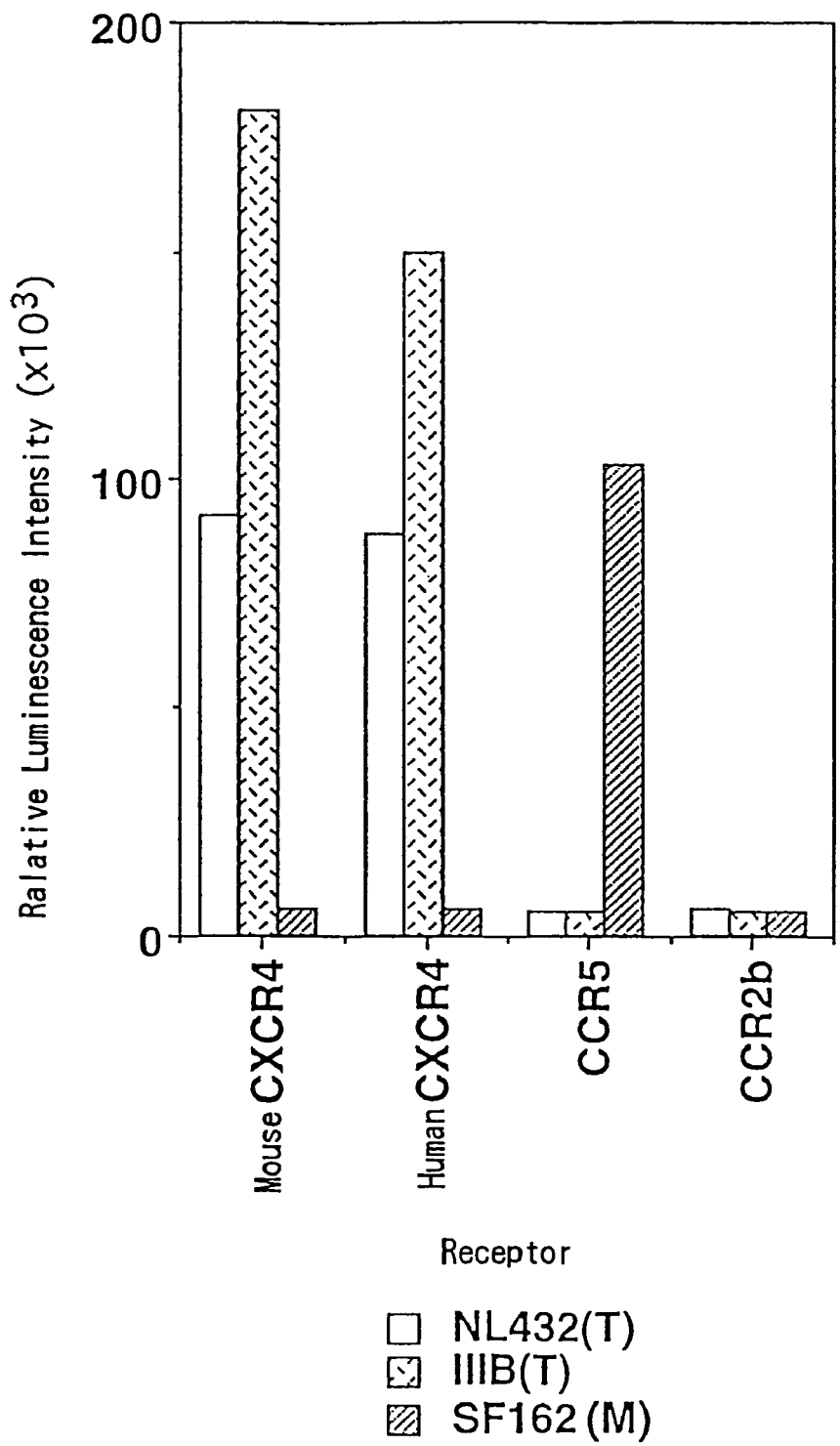
FIG. 11 is a graph showing that a murine CXCR4 supports an infection with a human T-cell-line-tropic HIV-1 virus. U87MG cells (C) are transfected with a human CD4, and each of chemokine receptors (murine CXCR4, human CXCR4, human CCR5, and human CCR2b). The resulting transfected cells are subjected to infection with each of NL432 strain, IIIB strain and SF162 strain of HIV-1. A cell lysate of each of the resulting infected cells is then subjected to β-gal assay.

On the other hand, with SF162, the SW480 expressing a human CCR5 and a human CD4 was infected, but cells expressing a murine CXCR4 and a human CD4, and cells expressing a human CXCR4 and a human CD4 were not infected therewith. In addition, similar results were obtained even when the HOS cells or the U87MG cells were used instead of the SW480 cells (FIG. 10 and FIG. 11). Thus, it was suggested that a murine CXCR4 supports the entry of a T-cell-line-tropic HIV-1 into target cells, and that it does not affect the DNA synthesis of a provirus, the integration to a genomic DNA or the viral expression in human cells.

Figure 12:
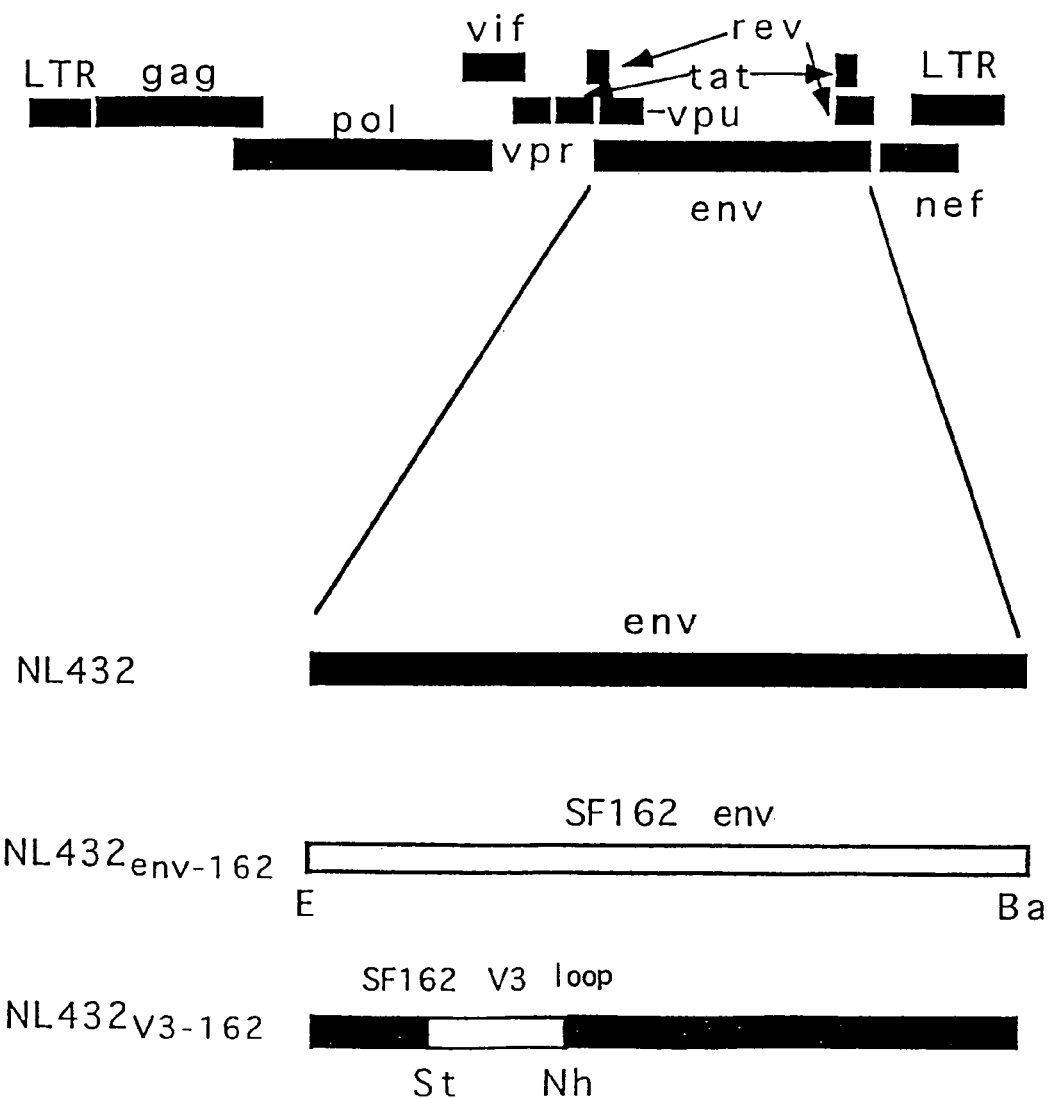
FIG. 12 is a schematic view showing the structure of chimeric provirus clone, wherein env or V3 loop of SF162 is incorporated into a provirus DNA of NL432, which is a human T-cell-line-tropic HIV-1 strain, wherein E denotes EcoRI; Ba denotes BamHI; St denotes StuI; and Nh denotes NheI.

Incidentally, there was clarified that the HIV-1 entry mediated by a human CXCR4 was inhibited by a monoclonal antibody against the V3 loop of an env protein. Accordingly, we have studied whether the V3 loop of the env protein (gpl120) (of a T-cell-line-tropic virus strain) is also required for a murine CXCR4-mediated HIV-1 entry in order to confirm the function of a murine CXCR4 is similar to that of a human CXCR4. For this purpose, the SW480 cells expressing a human CD4 and a chemokine receptor were subjected to infection with NL432env-162 or NL432V3-162 which is the chimera virus clone of NL432 and SF162. As shown in FIG. 12, NL432env-162 is a provirus clone in which the env region of a T-cell-line-tropic virus strain NL432 is substituted with that of a monocyte-tropic HIV-1 strain SF162, and NL432V3-162 is a provirus clone in which the V3 loop of the env of NL432 is substituted with that of SF162. The SW480 cells expressing a murine CXCR4 and a human CD4 were infected with NL432, but these cells were not infected with NL432env-162 or NL432V3-162 (FIG. 13).

Figure 13:
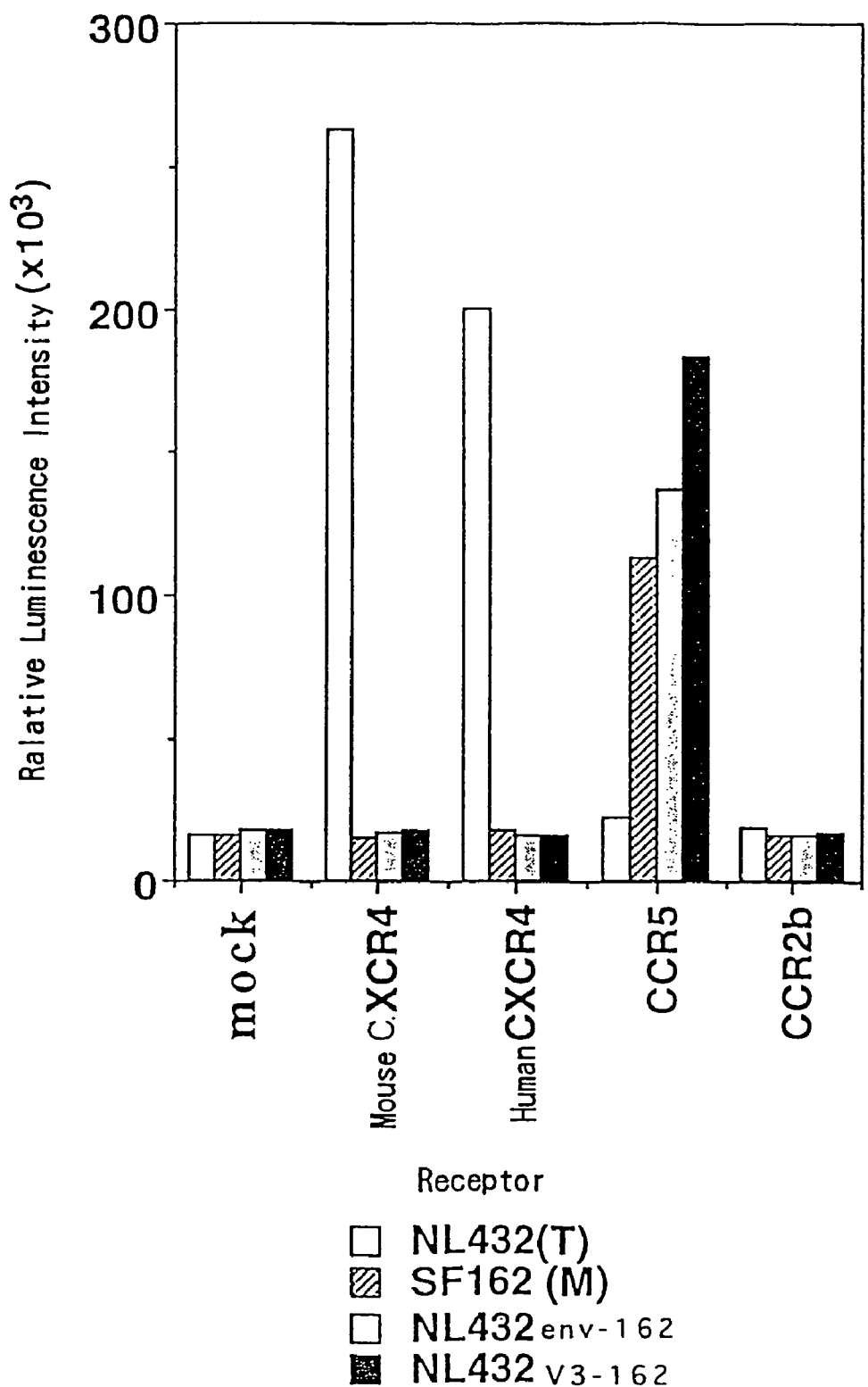
FIG. 13 is a diagram showing that a V3 loop of an envelope protein gp 120 is essential in an entry of HIV-1 via a murine CXCR4. The SW480 cells expressing the human CD4 and the receptors shown in the figure are subjected to infection with NL432 strain and SF162 strain of HIV-1, and NL432 env-162 and NL432 V3-162, which are chimeric provirus clones.

On the other hand, the SW480 cells expressing a human CCR5 and a human CD4 were infected with NL432env-162 and with NL432V3-162 (FIG. 13). It was clarified from the results that in the case of a murine CXCR4, a V3 loop of an NL432 env is also required for the viral entry in the same manner as the human CXCR4.

Discussion

From the studies described above, there has been clarified that the murine CXCR4 supports the cell membrane fusion mediated by a T-cell-line-tropic HIV-1 env and the infection with a T-cell-line-tropic HIV-1. These results suggest that the murine CXCR4 is not a species-specific barrier against the infection with an HIV-1. In the existing studies, there has been clarified even if a human CD4 were expressed in a cell line from murine lymphocytes or non-lymphocytes such as NIH3T3 or T-cell clone 3DT, the HIV-1 is adsorbed but not allowed to enter. One of the interpretations of these results is that the CXCR4 is not expressed on the surface of the murine cells which have expressed a human CD4. In fact, a murine PBSF/SDF-1 stimulation does not induce the change in the intracellular calcium level in the NIH3T3 cells. Nevertheless, the murine CXCR4 is expressed in thymocytes in which both of CD4 and CD8 are positive as well as in thymocytes in which either CD4 or CD8 is positive. Therefore, it is important (in order to invalidate the interpretation described above) to determine whether or not the 3DT cells used in the experiment express CXCR4.

In a recent study, there has been clarified that a murine homologue (murine CCR5) of a human CCR5, which is a receptor for a monocyte-tropic HIV-1, gives no support to an HIV-1 entry. This result suggests that there is a difference in the species-specificity between a receptor for a monocyte-tropic HIV-1 and a receptor for a T-cell-line-tropic HIV-1. This difference may be due to the fact that an amino acid sequence of CXCR4 is highly conserved in between the species, as compared to those of other chemokine receptors including CCR5. The amino acid sequence of a murine CXCR4 has a 90% identity with that of a human CXCR4, while a CCR5 and a CXCR2 exhibit only 82% and 71% identity, respectively, between the murine and human sequences. This inter-species high conservation of CXCR4 reflects the fact that PBSF/SDF-1, which is a CXCR4 ligand, has a unique function as compared to other chemokines such as MIP-1α, MIP-β and RANTES, which are CCR5 ligands. In contrary to the understanding that the chemokines other than PBSF/SDF-1 are involved in the chemotaxis of leukocytes in inflammation, PBSF/SDF-1 has a function essential for a biological development, such as hematopoiesis and cardiogenesis.

From the existing study results and from the facts that the production efficiency of virus particles is low as compared to that of human cells, even though a murine cell line NIH3T3 expressing a human CD4 and a chemokine receptor supports an HIV-1 entry, the murine cells may lack some intracellular molecules required for the replication of an HIV-1. However, an HIV-1-infected model mouse will be developed by generation of a transgenic mouse in which a human gene, which is a molecule causing a species-specific barrier, is introduced. Our results revealed the fact that it is not necessary to introduce a human CXCR4 gene into an HIV-1-infected model mouse. In addition, since an in vivo expression of CXCR4 is more apt to study the initiation and the progress of the transition from a monocyte-tropic HIV-1 to a T-cell-line-tropic HIV-1 which leads to an onset of AIDS, there is provided valuable information for the development of an animal model for simulation of an entire process of an HIV-1 infection.

INDUSTRIAL APPLICABILITY

According to the present invention, there can be provided a novel murine CXC chemokine receptor gene; a polypeptide encoded by the gene; an expression vector carrying the gene; a transformant harboring the expression vector; a monoclonal antibody against the polypeptide; a method for producing the polypeptide using the transformant; and a method of screening an agonist or antagonist of the polypeptide and also a method of screening an HIV-1 infection inhibitor, each of which is useful in studies of a therapeutic agent for AIDS and the functional mechanism of HIV-1 infection.

The invention claimed is:

1. An isolated polypeptide having an activity of a receptor that binds to a murine PBSF/SDF-1, wherein said polypeptide comprises the sequence of SEQ ID NO: 2.

2. The isolated polypeptide of claim 1, said polypeptide is encoded by a murine pre-B-cell line DW34 genome.

* * * * *